(12) United States Patent
Mongiat et al.

(10) Patent No.: US 7,101,536 B2
(45) Date of Patent: Sep. 5, 2006

(54) UV-PROTECTION FORMULATIONS

(75) Inventors: Sébastien Mongiat, Sierentz (FR); Cyrille Deshayes, Rosenau (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 509 days.

(21) Appl. No.: 10/452,234

(22) Filed: May 30, 2003

(65) Prior Publication Data

US 2003/0235539 A1 Dec. 25, 2003

(30) Foreign Application Priority Data

Jun. 3, 2002 (EP) ................... 02405443

(51) Int. Cl.
- *A61Q 17/04* (2006.01)
- *A61Q 17/00* (2006.01)
- *A61Q 19/00* (2006.01)
- *A61K 8/00* (2006.01)
- *A61K 8/02* (2006.01)

(52) U.S. Cl. .................. 424/59; 424/60; 424/400; 424/401

(58) Field of Classification Search .................. 424/59, 424/60, 400, 401
See application file for complete search history.

(56) References Cited

U.S. PATENT DOCUMENTS 6,217,852 B1 * 4/2001 Gildenberg et al. ............ 424/59

FOREIGN PATENT DOCUMENTS

| FR | 2001768 | 12/1969 |
|----|---------|---------|
| GB | 1538903 | 1/1979 |
| WO | 98/22447 | 5/1998 |

OTHER PUBLICATIONS

Derwent Abstr. 1983-778700 [40] for FR 2001768 (1969).

* cited by examiner

*Primary Examiner*—Shelley A. Dodson
(74) *Attorney, Agent, or Firm*—Kevin T. Mansfield

(57) ABSTRACT

The present invention relates to new UV-protection formulations with improved stability in respect to crystallisation, characterized in that a compound of formula (1) or a mixture thereof

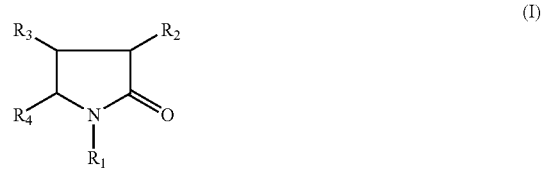

wherein
$R_1$ is substituted or unsubstituted $C_6$–$C_{12}$alkyl,
$R_2$, $R_3$ and $R_4$ are independently from each other hydrogen; substituted or unsubstituted $C_1$–$C_4$alkyl, preferably hydrogen; unsubstituted $C_1$–$C_2$alkyl or substituted $C_1$–$C_2$alkyl, more preferably hydrogen.
is added to the UV-protection formulation.

15 Claims, No Drawings

UV-PROTECTION FORMULATIONS

The present invention relates to new UV-protection formulations with improved stability in respect to crystallisation.

Most UV-protection formulations begin to crystallize after a relatively short period. The crystallization affects the efficiency of the UV-protection formulation. This phenomenon is increased at higher concentration of the UV absorber in the formulation.

Surprisingly, by the addition of certain pyrrolidone derivates the crystallisation of the UV-absorber formulation is hindered or at least strongly slowed down.

The invention relates also to an UV-protection formulation comprising a compound of formula (I) or a mixture thereof

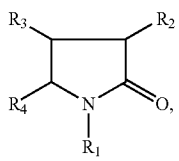

(I)

wherein
$R_1$ is substituted or unsubstituted $C_6$–$C_{12}$alkyl,
$R_2$, $R_3$ and $R_4$ are independently from each other hydrogen; substituted or unsubstituted $C_1$–$C_4$alkyl, preferably hydrogen; unsubstituted $C_1$–$C_2$alkyl or substituted $C_1$–$C_2$alkyl, more preferably hydrogen.

All alkyl groups present may be linear or branched.

Suitable substituents for the alkyl groups are for example Cl, Br, F, OH, CN, $SO_3H$, COOH, $NH_2$ and $N(alkyl)_2$.

A more preferred embodiment of the invention relates to an UV-protection formulation comprising a compound of formula (Ia)

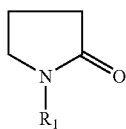

(Ia)

wherein $R_1$ is substituted or unsubstituted $C_6$–$C_{12}$alkyl.

The UV-protection formulation comprises preferably from 0.1 weight-% (wt-%) up to 10 wt-% of a compound of formula (I) or formula (Ia) or a mixture thereof. All weight percentages relate always to the total weight of the UV-protection formulation.

More preferably the UV-protection formulation comprises from 0.5 wt-% up to 5 wt-% of a compound of formula (I) or formula (Ia) or a mixture thereof.

In addition, the invention relates also to an UV protection formulation comprising additionally an ether or polyether compound or a mixture thereof.

Such an ether compound can be
(i) aliphatic such as A-O-B,
wherein A and B are independently from each other $C_1$–$C_{10}$alkyl; $C_1$–$C_4$alkylene-O—$C_1$–$C_8$alkyl or $C_1$–$C_4$alkylene-O—($C_1$–$C_4$alkylene-O—$)_{14}$ $C_1$–$C_8$alkyl, wherein the alkyl and alkylene groups may be linear or branched and optionally substituted by at least one substituent of the group consisting of CN, OH, halogen or $NH_2$;
(ii) methoxycinnamate derivates such as for example diethanoleamine-methoxycinnamate or glyceryl ethylhexanoate dimethoxycinnamate; or
(iii) cyclic such as for example such as tetrahydrofuran or 1,3-dioxolane; or
(iv) silicone-containing, such siloxane ether can be for example $Si(OC_1$–$C_4alkyl)_n(C_1$–$C_{10}alkyl)_{4-n}$, wherein n is 1, 2 or 3 and the alkyl groups may linear or branched.

Preferred ether compounds are $C_1$–$C_4$alkyl-O—$C_1$–$C_4$alkyl; $C_1$–$C_2$alkyl-O—$C_1$–$C_2$alkylene-O—$C_1$–$C_2$alkyl; $C_1$–$C_2$alkyl-O—$C_4$–$C_8$alkyl; $Si(OC_1$–$C_2alkyl)_3$ $(C_4$–$C_{10}alkyl)$; $C_1$–$C_4$alkyl-O—$(CF_2)_{1-3}$ $CF_3$; $C_1$–$C_4$alkyl-O—$(CF_2)_{1-3}CF(CF_3)_2$; $C_1$–$C_2$alkyl-O—$CH_2CH(CH_3)$—O—$CH(CH_3)CH_2$—OCH3; $C_1$–$C_{10}$alkyl-O—$CH_2CH(OH)C_1$–$C_2$alkyl; diethanoleamine-methoxycinnamate; glyceryl ethylhexanoate dimethoxycinnamate; tetrahydrofuran or 1,3-dioxolane.

The UV protection formula comprise such ethers in an amount up to about 20 wt-%, preferably from about 2.5 up to about 10 wt-%.

Suitable UV absorbers for UV-protection formulations have the following formulae (II) to (XI)

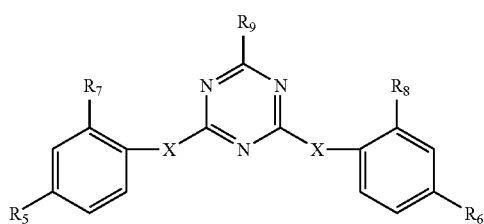

(II)

in which
X is —$NR_{10}$— or a direct bond, in which
$R_{10}$ is hydrogen; $C_1C_4$alkyl or substituted $C_1.C_4$alkyl,
$R_5$ and $R_6$, independently of one another, are $OC_3$—$C_{18}$alkyl; $OC_2$–$C_{18}$alkenyl; a radical of the formula —$CH_2$—$CH($—$OH)$—$CH_2$—O-$T_1$; $COOC_3$–$C_{18}$alkyl; $NR_{10}OC_3$–$C_{18}$alkyl, wherein
$T_1$ is hydrogen or $C_1$–$C_8$alkyl and
$R_{10}$ is as defined above, or
$R_5$ and $R_6$ are a radical of the formula (1a)

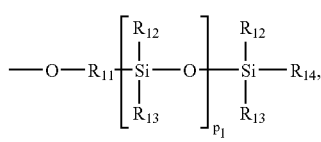

in which
$R_{11}$ is a direct bond; a straight-chain or branched $C_1$–$C_4$alkylene radical or a radical of the formula —$C_{m_1}H_{2m_1}$— or —$C_{m_1}H_{2m_1}$—O—,
$R_{12}$, $R_{13}$ and $R_{14}$, independently of one another, are $C_1$–$C_{18}$alkyl; $C_1$–$C_{18}$alkoxy or a radical of the formula

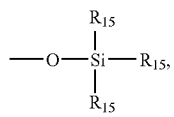

$R_{15}$ is $C_1$–$C_5$alkyl, each $m_1$ is independently of one another 1 to 4, $p_1$ is 0 or a number from 1 to 5, $R_7$ and $R_8$ are independently from each other H; OH or $OC_1$–$C_5$alkyl, $R_9$ is $COOC_3$–$C_{18}$alkyl; $NR_{10}OC_3$–$C_{18}$alkyl, wherein $R_{10}$ is as defined above, or $R_9$ is a radical of the formula

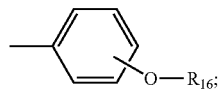 (1b)

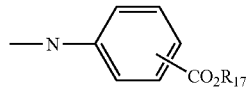 (1c)

or of the formula

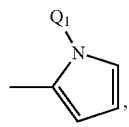 (1d)

wherein $R_{16}$ is hydrogen; $C_1$–$C_{10}$alkyl; —$(CH_2CHR_{18}$—$O)_{n1}$—$R_{17}$ or a radical of the formula

—$CH_2$—$CH(-OH)$—$CH_2$—$O$-$T_1$ $R_{17}$ is hydrogen; M; $C_1$–$C_5$alkyl or a radical of the formula —$(CH_2)_{m2}$—$O$-$T_1$, $R_{18}$ is hydrogen or methyl, $T_1$ is hydrogen or $C_1$–$C_8$alkyl, $Q_1$ $C_1$–$C_{18}$alkyl, M is a metal cation, $m_2$ is 1 to 4, and $n_1$ is 1–16;

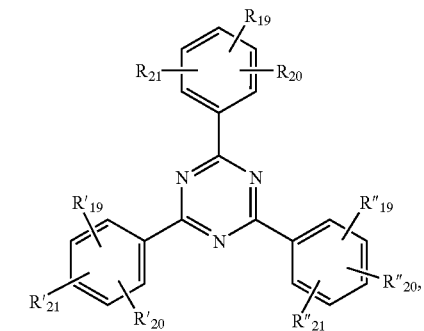

wherein $R_{19}$, $R_{19}'$, $R_{19}''$, $R_{20}$, $R_{20}'$ and $R_{20}''$ are each independently of the other hydrogen; hydroxy; $C_1$–$C_{12}$alkyl; $OC_1$–$C_{12}$alkyl; $OC_2$–$C_{18}$alkenyl or $OC_1$–$C_4$alkylene-phenyl, and $R_{21}$, $R_{21}'$ and $R_{21}''$ are each independently of the other $C_1$–$C_{12}$alkyl or $C_1$–$C_{12}$alkoxy;

(IV)

[Structure IV as shown]

wherein $R_{22}$ and $R_{23}$ independently from each other signify $C_1$–$C_{12}$alkyl;

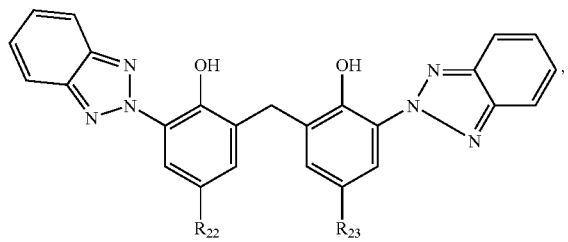

in which $R_{24}$ and $R_{25}$, independently from each other, are $C_1$–$C_{18}$alkyl or

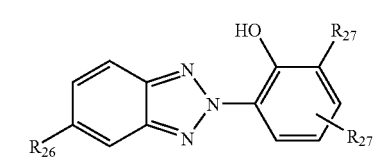

in which $R_{26}$ is $C_1$–$C_{18}$alkyl or hydrogen, and
$R_{27}$ is $C_1$–$C_{18}$alkyl, optionally substituted by phenyl;

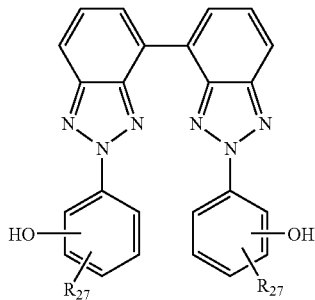

(VII)

which $R_{27}$ has its previous significance;

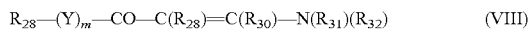

(VIII)

in which $R_{28}$ is $C_1$–$C_{18}$alkyl or phenyl optionally substituted by one, two or three substituents selected from OH, $C_1$–$C_{18}$alkyl, $C_1$–$C_{18}$alkoxy or CO—$OR_{33}$, in which
$R_{33}$ is $C_1$–$C_{18}$alkyl,
$R_{29}$, $R_{30}$, $R_{31}$ and $R_{32}$ are the same or different and each is $C_1$–$C_{18}$alkyl or hydrogen,
Y is N or O, and
m is 0 or 1;

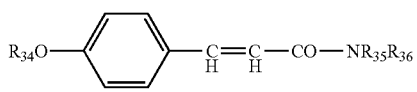

(IX)

in which $R_{34}$ is hydroxy or $C_1$–$C_4$alkoxy,
$R_{35}$ is hydrogen or $C_1$–$C_4$alkyl, and
$R_{36}$ is —(CONH)$_m$-phenyl in which
 m has its previous significance and the phenyl group is optionally substituted by one, two or three substituents selected from OH, $C_1$–$C_{18}$alkyl, $C_1$–$C_{18}$alkoxy or $COOR_{33}$ in which $R_{33}$ has its previous significance;

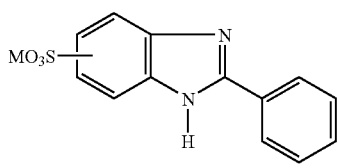

(X)

in which

M is hydrogen, an alkali metal, an alkaline earth metal or zinc;

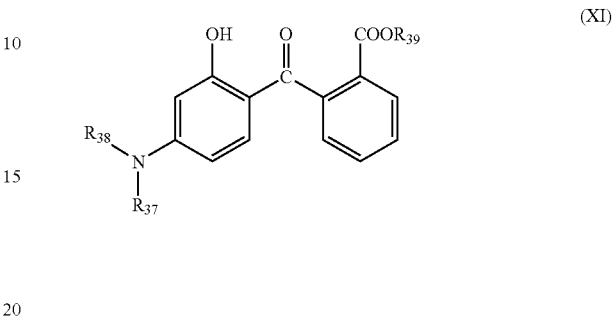

(XI)

wherein $R_{37}$ and $R_{38}$ signify independently from each other H; unsubstituted $C_1$–$C_{20}$alkyl; substituted $C_1$–$C_{20}$alkyl; unsubstituted $C_3$–$C_{10}$-cycloalkyl; substituted $C_3$–$C_{10}$-cycloalkyl; unsubstituted $C_3$–$C_{10}$-cycloalkenyl or substituted $C_3$–$C_{10}$-cycloalkenyl, or $R_{37}$ and $R_{38}$ form together with the nitrogen atom to which they are bound a 5 or 6 membered ring, and $R_{39}$ signifies unsubstituted $C_1$–$C_{20}$alkyl or substituted $C_1$–$C_{20}$alkyl.

All alkyl groups present may be linear or branched.
All alkenyl groups present may be linear or branched.
All alkoxy groups present may be linear or branched.
The alkyl-, alkenyl-, cycloalkyl-, cycloalkenyl-, and alkoxy-radicals are preferably substituted by Cl, Br, F, OH, CN, SO$_3$H, COOH, NH$_2$ and N(alkyl)$_2$.

Preferred UV-protection formulations comprise compounds according to formula (II), (III) and/or formula (XI).

More preferred UV-protection formulations comprise compounds according to formula (IIa)

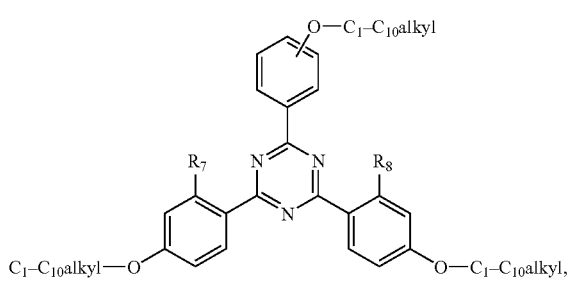

(IIa)

wherein, $R_7$ and $R_8$ are independently from each other H; OH or $OC_1$–$C_5$alkyl.

Further more preferred UV-protection formulations comprise compounds according to formula (IIb)

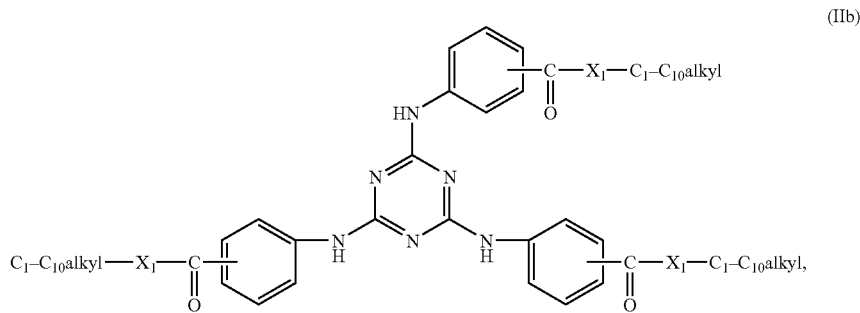

wherein $X_1$ signifies —O— or —NH—.

Further more preferred UV-protection formulations comprise compounds according to formula (IIIa)

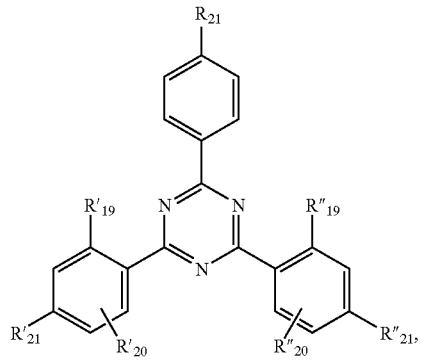

wherein $R_{19}'$, $R_{19}''$, $R_{20}'$ and $R_{20}''$ are independently from each other hydrogen; hydroxy; $C_1$–$C_{12}$alkyl or $C_1$–$C_{12}$alkyoxy, and $R_{21}$, $R_{121}$ and $R_{121}$ are independently from each other hydroxy; $C_1$–$C_{12}$alkyl or $C_1$–$C_{12}$alkoxy.

Further more preferred UV-protection formulations comprise compounds according to formula (IIIb)

wherein $R_{19}$, $R_{19}'$ and $R_{19}''$ are independently from each other hydroxy or $C_1$–$C_{12}$alkyoxy, and $R_{20}$, $R_{20}'$ and $R_{20}''$ are independently from each other hydroxy or $C_1$–$C_{12}$alkyl, and $R_{21}$, $R_{21}'$ and $R_{12}''$ are independently from each other hydrogen or $C_1$–$C_{12}$alkyl.

Further more preferred UV-protection formulations comprise compounds according to formula (XIa)

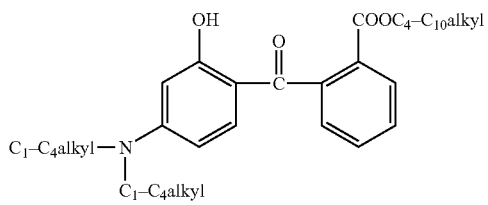

Examples of suitable UV absorbers for UV-protection formulations are as follows

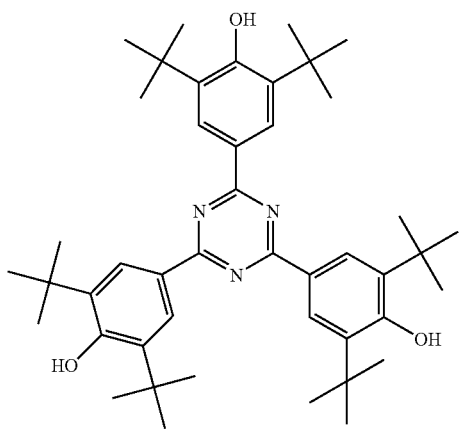
(1)
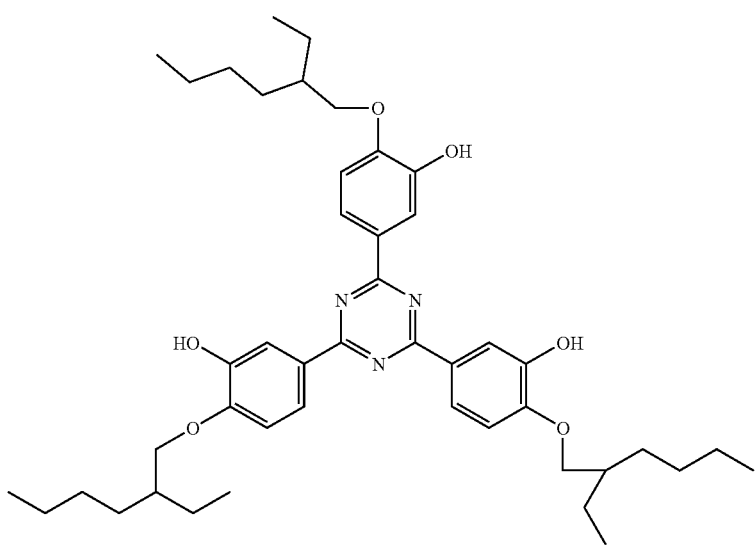
(2)
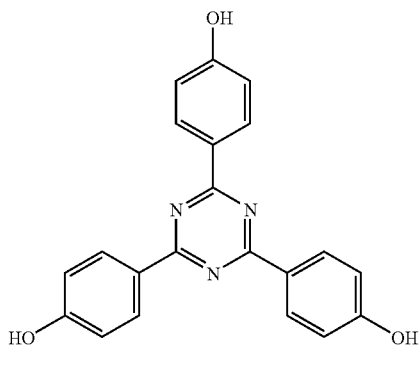
(3)
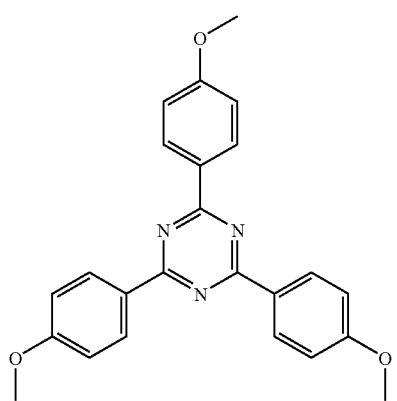
(4)

-continued
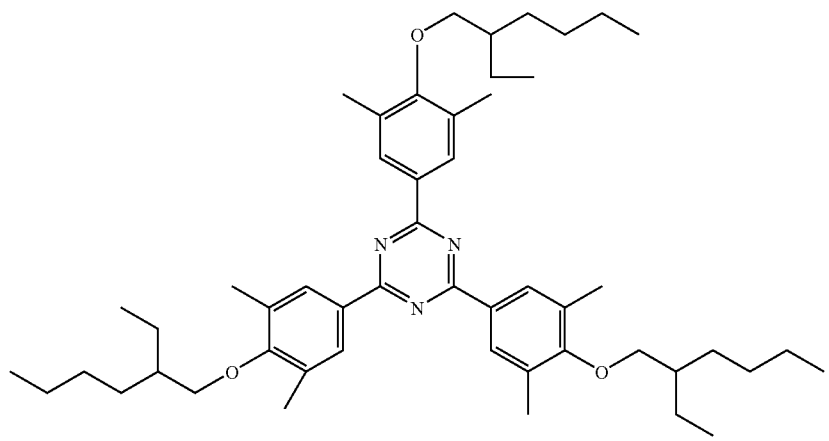
(5)
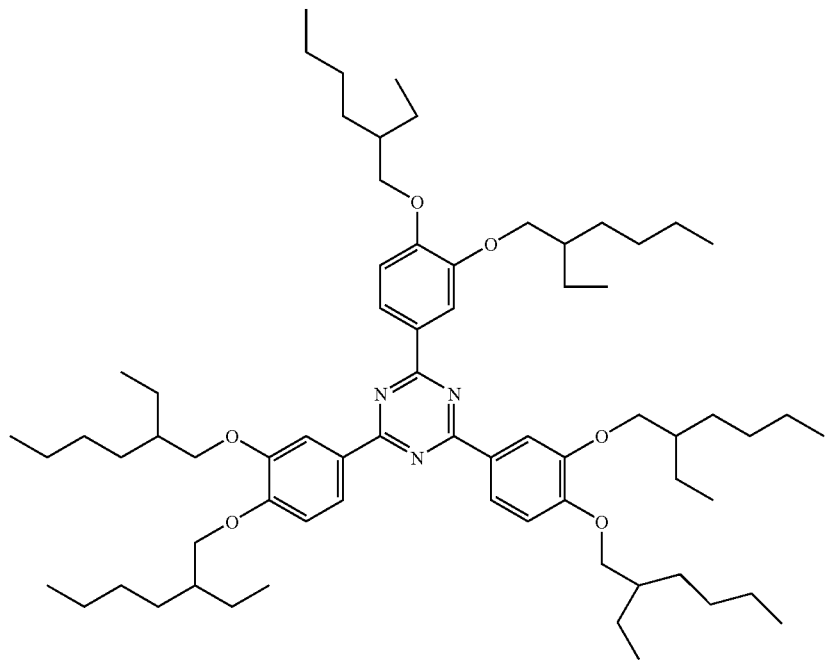
(6)
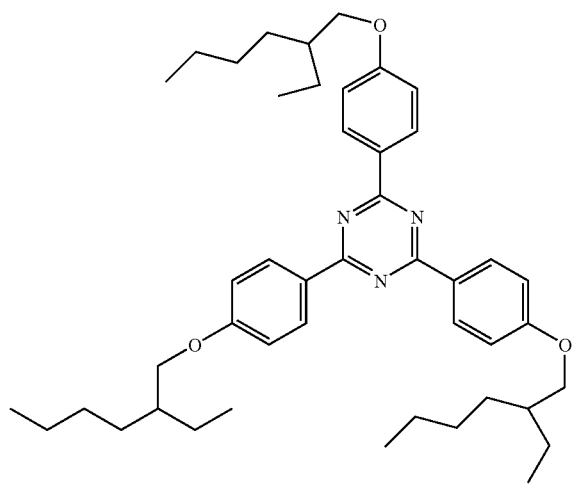
(7)

-continued
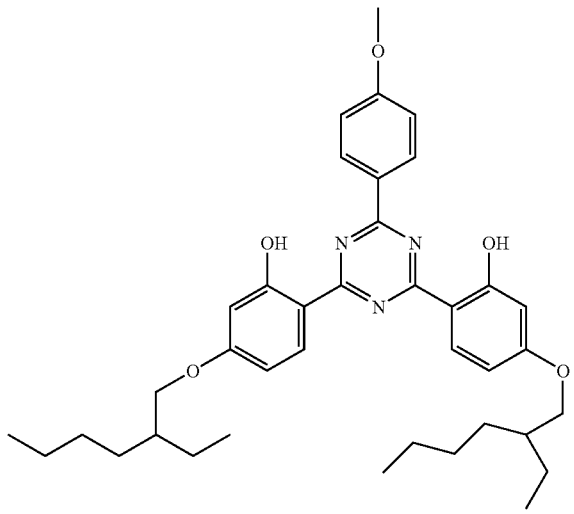
(8)
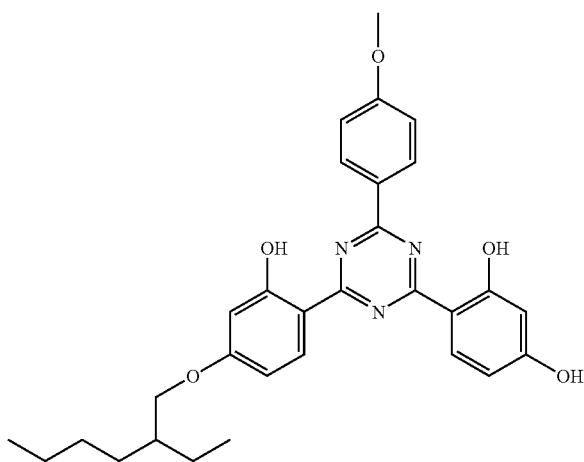
(9)
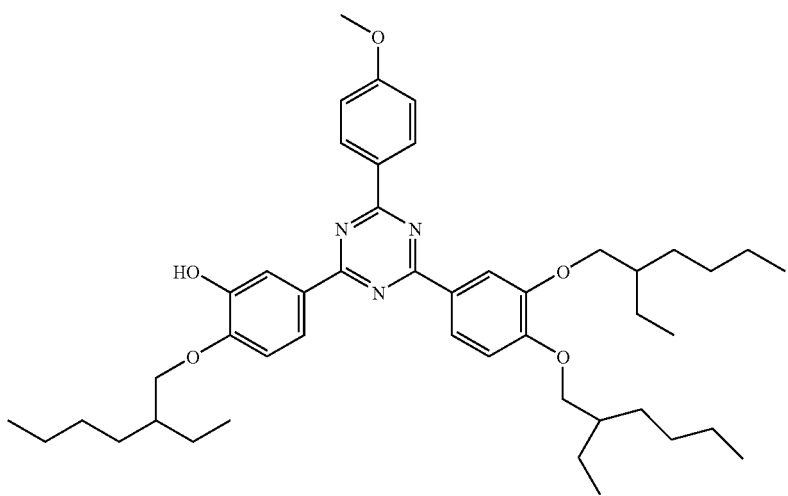
(10)

-continued
(11)
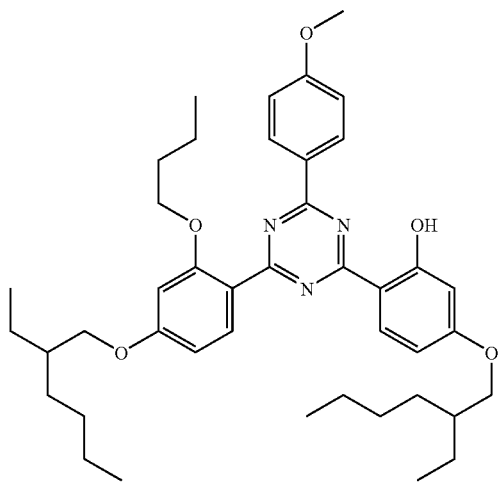
(12)
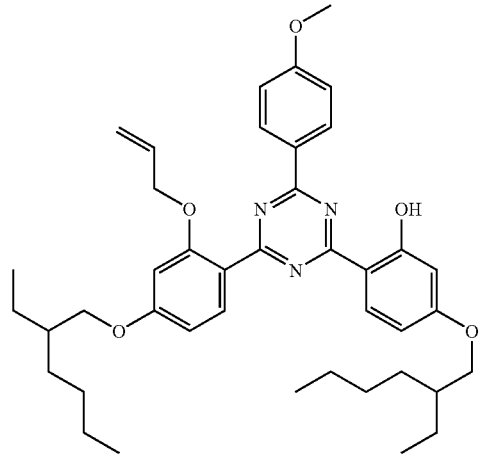
(13)
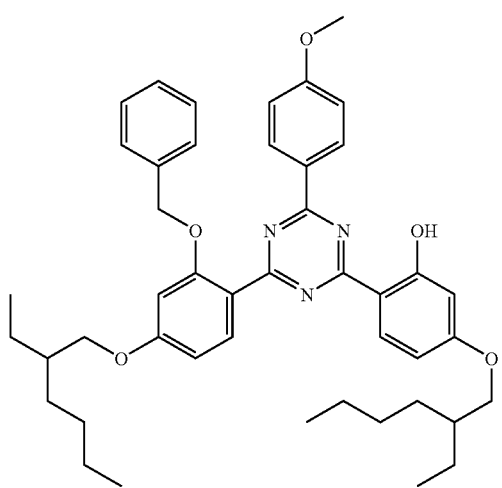
(14)
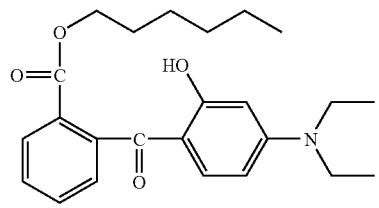
(15)
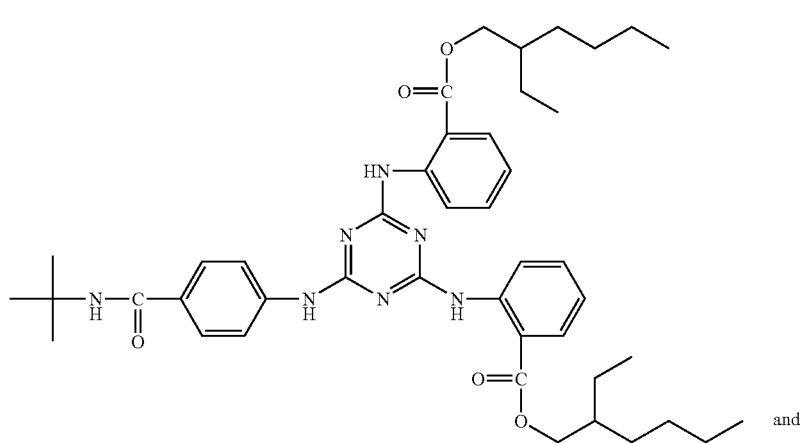
and

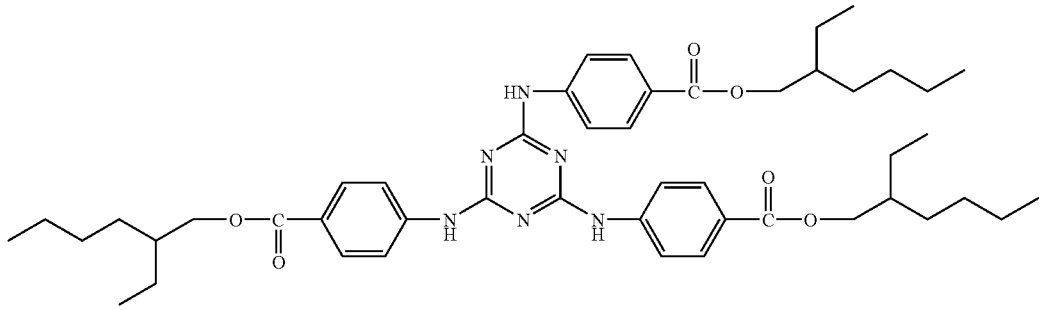

(16)

The UV absorbers can be used either in the dissolved state or in the micronised state.

Any known process suitable for the preparation of microparticles can be used for the preparation of the micronised UV absorbers, for example:

wet-grinding with a hard grinding medium, for example zirconium silicate and a protective surfactant or a protective polymer in water or in a suitable organic solvent;

spray-drying from a suitable solvent, for example aqueous suspensions or suspensions containing organic solvents, or true solutions in water, ethanol, dichloroethane, toluene or N-methylpyrrolidone etc.

by the expansion according to the RESS process (Rapid Expansion of Supercritical Solutions) of supercritical fluids (e.g. $CO_2$) in which the UV filter or filters is/are dissolved, or the expansion of fluid carbon dioxide together with a solution of one or more UV filters in a suitable organic solvent;

by reprecipitation from suitable solvents, including supercritical fluids (GASR process=Gas Anti-Solvent Recrystallisation/PCA process=Precipitation with Compressed Anti-solvents).

As grinding apparatus for the preparation of the micronised organic UV absorbers there may be used, for example, a jet mill, ball mill, vibratory mill or hammer mill, preferably a high-speed mixing mill. The grinding is preferably carried out with a grinding aid, for example an alkylated vinylpyrrolidone polymer, a vinylpyrrolidone/vinyl acetate copolymer, an acyl glutamate, an alkyl polyglucoside, ceteareth-25 or a phospholipid.

The micronised UV absorbers so obtained usually have an average particle size that is from 0.02 to 2 µm, preferably from 0.05 to 1.5 µm, and more especially from 0.1 to 1.0 µm.

The UV absorbers can also be used dry in powder form. For that purpose the UV absorbers are subjected to known grinding methods, such as vacuum atomization, countercurrent spray-drying etc. Such powders have a particle size of from 0.1 µm to 2 µm. To avoid the occurrence of agglomeration, the UV absorbers can be coated with a surface-active compound prior to the pulverisation process, for example with an anionic, non-ionic or amphoteric surfactant, e.g. a phospholipid or a known polymer, such as PVP, an acrylate etc.

The UV-protection formulation contains, for example, from 0.05 wt-% to 40 wt-%, preferably from 0.1 to 20 wt-% and especially from 0.5 wt-% to 10 wt-%, based on the total weight of the composition, of one or more UV absorbers.

The UV-protection formulation can be prepared by physically mixing the UV absorber(s) with the adjuvant using customary methods, for example by simply stirring together the individual components, especially by making use of the dissolution properties of already known cosmetic UV absorbers, for example octyl methoxy cinnamate, salicylic acid isooctyl ester, etc. The UV absorber can be used, for example, without further treatment, or in the micronised state, or in the form of a powder.

In addition to the above-described UV absorbers, the UV-protection formulation can also contain one or more than one further UV protective of the following substance classes: (Abbreviations T: table, R: row, Comp: compound, Ex: compound(s) of patent example, p: page)

| | |
|---|---|
| EP 895776 | Comp. in Rows 48–58, p 3; R 25 + 33, p 5 |
| WO 9220690 | Polymeric comp in Examples 3–6 |
| EP 1000950 | Comp. in Table 1, pp 18–21 |
| EP 1060734 | T 1–3, pp 11–14 |
| EP 1059082 | Ex 1; T 1, pp 9–11 |
| EP 1008586 | Ex 1–3, pp 13–15 |
| EP 1005855 | T 3, p 13 |
| EP 1129695 | Ex 1–7, pp 13–14 |
| EP 967200 | Ex 2; T 3–5, pp 17–20 |
| EP 945125 | T 3 a + b, pp 14–15 |
| EP 924246 | T 2, p 9 |
| EP 911020 | T 2, p 11–12 |
| EP 916335 | T 2–4, pp 19–41 |
| EP 852137 | T 2, pp 41–46 |
| EP 858318 | T 1, p 6 |
| EP 826361 | T 1, pp 5–6 |
| EP 503338 | T 1, pp 9–10 |
| WO 9301164 | T 1 + 2, pp 13–22 |
| EP 823418 | Ex 1–4, pp 7–8 |
| WO 9714680 | Ex 1–3, p 10 |
| EP 1027883 | Compound VII, p 3 |
| EP 832641 | Ex 5 + 6 p 7; t 2, p 8 |
| US 5338539 | Ex 1–9, pp 3 + 4 |
| EP 517103 | Ex 3, 4, 9, 10 pp 6–7 |
| EP 1123934 | T 3, p 10 |
| EP 1027883 | Comp I–VI, p 3 |
| EP 969004 | Ex 5, T 1, pp 6–8 |
| US 5801244 | Ex 1–5, pp 6–7 |
| EP 832642 | Ex 22, T 3 pp, 10–15; T 4, p 16 |
| US 5346691 (EP 570838) | Ex 40, p 7; T 5, p 8 |
| EP 517104 | Ex 1, T 1, pp 4–5; Ex 8, T 2, pp 6–8 |
| WO 200149686 | Ex 1–5, pp 16–21 |
| EP 944624 | Ex 1 + 2, pp 13–15 |
| EP 933376 | Ex 1–15, pp 10–21 |
| EP 863145 | Ex 1–11, pp 12–18 |
| EP 780382 | Ex 1–11, pp 5–7 |
| EP 626950 | |
| EP 1081140 | Ex 1–9, pp 11–16 |
| WO 9217461 | Ex 1–22, pp 10–20 |
| WO 0168047 | Tables on pp 85–96 |
| EP 613893 | Ex 1–5 + 15, T 1, pp 6–8 |
| EP 1064922 | Compounds 1–34, pp 6–14 |

-continued

| EP 1028120 | Ex 1–5, pp 5–13 |
| EP 1008593 | Ex 1–8, pp 4–5 |
| EP 669323 | Ex 1–3, p 5 |
| EP 1108712 | 4,5-Dimorpholino-3-hydroxypyridazine |
| JP 2000319629 | CAS Regno. 80142-49-0, 137215-83-9, 307947-82-6 |
| EP 420707 B1 | Ex 3, p 13 (80142-49-0) |
| US 5635343 | |
| EP 1167358 | |

In addition to the triazine UV absorbers described in WO 9822447, the cosmetic formulations can also contain one or more than one further UV protective of the following substance classes:

p-aminobenzoic acid derivatives, for example 4-dimethylaminobenzoic acid 2-ethylhexyl ester;

salicylic acid derivatives, for example salicylic acid 2-ethylhexyl ester;

benzophenone derivatives, for example 2-hydroxy-4-methoxybenzophenone and its 5-sulfonic acid derivative;

dibenzoylmethane derivatives, for example 1-(4-tert-butylphenyl)-3-(4-methoxyphenyl)propane-1,3-dione;

diphenylacrylates, for example 2-ethylhexyl 2-cyano-3,3-diphenylacrylate, and 3-(benzofuranyl) 2-cyanoacrylate;

3-imidazol-4-ylacrylic acid and esters;

benzofuran derivatives, especially 2-(p-aminophenyl) benzofuran derivatives, described in EP-A-582 189, U.S. Pat. No. 5,338,539, U.S. Pat. No. 5,518,713 and EP-A-613 893;

polymeric UV absorbers, for example the benzylidene malonate derivatives described in EP-A-709 080;

cinnamic acid derivatives, for example the 4-methoxycinnamic acid 2-ethylhexyl ester and isoamyl ester or cinnamic acid derivatives described in U.S. Pat. No. 5,601,811 and WO 97/00851;

camphor derivatives, for example 3-(4'-methyl)benzylidene-bornan-2-one, 3-benzylidenebornan-2-one, N-[2(and 4)-2-oxyborn-3-ylidene-methyl)-benzyl] acryl-amide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;

hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethylhexyloxy)-2-hydroxy]-phenyl}-6-[4-(2-methoxyethylcarboxyl)-phenylamino]-1,3,5-triazine; 2,4-bis{[4-(tris(trimethylsilyloxy-silylpropyloxy)-2-hydroxy]-phenyl}-6-(4-methoxy-phenyl)-1,3,5-triazine; 2,4-bis{[4-(2"-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2"-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenyl-amino]-1,3,5-triazine;

benzotriazole compounds, for example 2,2'-methylene-bis(6-(2H-benzotriazol-2-yl)-4-(1,1,3,3-tetramethylbutyl)-phenol;

trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;

2-phenylbenzimidazole-5-sulfonic acid and salts thereof;

menthyl o-aminobenzoates;

physical sunscreens coated or not as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane CAS 9004-73-3), dimethicone, isopropyl titanium triisostearate (CAS 61417-49-0), metal soaps as magnesium stearate (CAS 4086-70-8), perfluoroalcohol phosphate as $C_{9-15}$ fluoroalcohol phosphate (CAS 74499-44-8; JP 5-86984, JP 4-330007)). The primary particle size is an average of 15 nm-35 nm and the particle size in dispersion is in the range of 100 nm-300 nm.

aminohydroxy-benzophenone derivatives disclosed in DE 10011317, EP 1133980 and EP 1046391 phenyl-benzimidazole derivatives as disclosed in EP 1167358

The UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

In addition to the above-mentioned pyrolidone and UV absorbing compounds UV, the UV-protection formulation may contain further adjuvants as described below.

The UV-protection formulation may be, for example, creams, gels, lotions, alcoholic and aqueous/alcoholic solutions, emulsions, wax/fat compositions, stick preparations, powders or ointments.

Water- and oil-containing emulsions. As water- and oil-containing emulsions (e.g. W/O, O/W, O/W/O and W/O/W emulsions or microemulsions) the UV-protection formulation contain from 0.1 wt-% up to 10 wt-% of at least one compound of formula (I) and, for example, from 0.1 wt-% to 30 wt-%, preferably from 0.1 wt-% to 15% wt-% and especially from 0.5 wt-% to 10% wt-%, based on the total weight of the composition, of one or more UV absorbers, from 1 wt-% to 60 wt-%, especially from 5 wt-% to 50 wt-% and preferably from 10 wt-% to 35 wt-%, based on the total weight of the composition, of at least one oil component, from 0 wt-% to 30 wt-%, especially from 1 wt-% to 30 wt-% und preferably from 4 wt-% to 20 wt-%, based on the total weight of the composition, of at least one emulsifier, from 10 wt-% to 90 wt-%, especially from 30 wt-% to 90 wt-%, based on the total weight of the composition, of water, and from 0 wt-% to 88.9 wt-%, especially from 1 wt-% to 50 wt-%, of further cosmetically acceptable adjuvants.

The oil phase can be chosen from the following substance groups without limiting the kind of lipophilic ingredient to those substances:

Fatty alcohols: Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of $C_{12}$–$C_{15}$ alcohols, acetylated lanolin alcohol, etc.

Esters of fatty acids: esters of linear $C_6$–$C_{24}$ fatty acids with linear $C_3$–$C_{24}$ alcohols, esters of branched $C_6$–$C_{13}$ carboxylic acids with linear $C_6$–$C_{24}$ fatty alcohols, esters of linear $C_6$–$C_{24}$ fatty acids with branched alcohols, especially 2-ethylhexanol, esters of hydroxycarboxylic acids with linear or branched $C_6$–$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Further oil components that can be used are dicarboxylic acid esters, such as diethylhexyl 2,6-naphthalate, di-n-butyl adipate, di(2-ethylhexyl)-adipate, di(2-ethylhexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$–$C_{24}$ fatty alcohols and/or Guerbet alcohols with aromatic carboxylic acids, saturated and/or unsaturated, especially benzoic acid, esters of $C_2$–$C_{12}$ dicarboxylic acids with linear or branched alcohols having from 1 to 22 carbon atoms or polyols having from 2 to 10 carbon atoms and from 2 to 6 hydroxy groups.

Natural or synthetic triglycerides including glyceryl esters and derivatives. Di- or tri-glycerides, based on $C_6$–$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides. Pearlescent waxes: Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon oils: mineral oil (light or heavy), petrolatum (yellow or white), microcrystalline wax, paraffinic and isoparaffinic compounds, hydrogenated isoparaffinic molecules as polydecenes, and polybutene, hydrogenated polyisobutene, squalane, isohexadecane, isododecane and others from plant and animal kingdom.

Silicones or siloxanes (organosubstituted polysiloxanes): dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes: dimethicone such as Dow Corning® 200 fluid, Mirasil® DM (Rhodia), dimethiconol. Cyclic silicone fluids: cyclopentasiloxanes volatiles such as Dow Corning® 345 fluid, Silbione® grade, Abil® grade. Phenyltrimethicone; Dow corning® 556 fluid. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

It is also suitable to use nonvolatile organopolysiloxane compounds as described for example in WO 94/21224. Such compounds improve the disentangling, softness and hold properties. Preferably, organopolysiloxane compounds are nonvolatile organopolysiloxane chosen from polyalkylsiloxanes, polyarylsiloxanes, polyalkylarylsiloxanes, silicone gums and resins or organomodified polysiloxanes, with the exception of polysiloxanes carrying polyethyleneoxy and/or polypropyleneoxy, or carboxylate or bisulfite, groups.

The organopolysiloxanes are nonvolatile organopolysiloxane oils or organosiloxane gum or resin organic solutions or alternatively emulsions or microemulsions containing these organopolysiloxanes.

Example of such nonvolatile organopolysiloxane compounds are polyalkylsiloxanes, mainly linear polydimethylsiloxanes: either,
containing end trimethylsilyl groups, such as, for example, and without implied limitation, Silbione oils of the 70047 series marketed by Rhône-Poulenc, 47 V 500,000 oil from Rhône-Poulenc or certain Viscasil® from General Electric, or
containing end trihydroxysilyl groups, such as the oils of the 48 V series from Rhone-Poulenc.

Mention may also be made, in this class of polyalkylsiloxanes, of polyalkylsiloxanes sold by the Company Goldschmidt under the names Abilwax® 9800 and Abilwax® 9801, which are polyalkyl($C_1$–$C_{20}$)siloxanes.

Mention may be made, among the polyalkylarylsiloxanes, of linear and/or branched polydimethylphenylsiloxanes or polydimethyldiphenylsiloxanes, with a viscosity of $10^{-5}$ to $5.10^{-2}$ m$^2$s$^{-1}$ at 25° C., such as, for example:

Rhodorsil® 763 oil from Rhône-Poulenc,

Silicone oils of the 70641 series from Rhône-Poulenc, such as Silicone 70641 V 30 and 70641 V 200 oils from Rhône-Poulenc, the product DC 556 Cosmetic Grad Fluid from Dow Corning, silicones of the PK series from Bayer, such as PK20, silicones of the PN and PH series from Bayer, such as PN 1000 and PH 1000, certain oils of the SF series from General Electric, such as SF 1250, SF 1265, SF 1154 and SF 1023, 618 V 25000 oil from Rhone-Poulenc.

The silicone gums in accordance with the present invention are polydiorganosiloxanes with a high molecular mass of between 200,000 and 1,000,000, used alone or as a mixture in a solvent chosen from polydimethylsiloxane (PDMS) oils, polyphenylmethylsiloxane (PPMS) oils, isoparaffins, methylene chloride, pentane, dodecane, tridecane, tetradecane or their mixtures.

Mention is made, for example, of the following compounds:

polydimethylsiloxane, optionally hydroxylated at the chain end,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)].

Mention may be made, for example, without implied limitation, of the following mixtures:

1) the mixtures formed from a polydimethylsiloxane hydroxylated at the chain end (Dimethiconol according to the CTFA nomenclature) and from a cyclic polydimethylsiloxane (Cyclomethicone according to the CTFA nomenclature), such as the product Q2 1401 sold by the Company Dow Corning;

2) the mixtures formed from a polydimethylsiloxane gum with a cyclic silicone, such as the product SF 1214 Silicone Fluid from General Electric, which is an SE 30 gum with a MW of 500,000 dissolved in SF 1202 Silicone Fluid (decamethylcyclopentasiloxane);

3) the mixtures of two PDMS of different viscosities, in particular of a PDMS gum and of a PDMS oil, such as the products SF 1236 and CF 1241 from the Company General Electric. The product SF 1236 is the mixture of an SE 30 gum defined hereinabove, with a viscosity of 20 m$^2$s$^{-1}$, and of an SF 96 oil, with a viscosity of $5.10^{-6}$ m$^2$s$^{-1}$ (15% of SE 30 gum and 85% of SF 96 oil). The product CF 1241 is the mixture of an SE 30 gum (33%) and of a PDMS (67%) with a viscosity of $10^{-1}$ m$^2$s$^{-1}$.

The organopolysiloxane resins which can be used in accordance with the invention are crosslinked siloxane systems containing the units: $R_2SiO_{2/2}$, $RSiO_{3/2}$ and $SiO_{4/2}$, in which R represents a hydrocarbon group having 1 to 6 carbon atoms or a phenyl group. The particularly preferred products among these are those in which R denotes a lower alkyl radical or a phenyl radical.

Mention may be made, among these resins, of the product sold under the name Dow Corning 593 or of those sold under the names Silicone Fluid SS 4230 and SS 4267 by the Company General Electric and which are "dimethyl/trimethylpolysiloxane".

The organomodified silicones in accordance with the present invention are silicones as defined above containing, in their general structure, one or a number of organofunctional groups directly attached to the siloxane chain or attached via a hydrocarbon radical.

Mention is made, for example, of the silicones containing:

a) fluorinated groups such as trifluoroalkyls, such as, for example, those sold by the Company General Electric under the names "FF 150 Fluorosilicone Fluid" or by the Company Shin Etsu under the names X-22-819, X-22-820, X-22-821 and X-22-822;

b) hydroxyacylamino groups, such as those described in European Patent Application EP342834 and in particular the silicone sold by the Company Dow Corning under the name Q2-8413;

c) thiol groups, as in the silicones X 2-8360 from Dow Corning or GP 72A and GP 71 from Genesee;

d) substituted or unsubstituted amino groups, as in GP4 Silicone Fluid from Geneses, GP 7100 from Genesee, Q2 8220 from Dow Corning, AFL 40 from Union Carbide or the silicone known as "Amodimethicone" in the CTFA dictionary;

e) hydroxylated groups, such as the polyorganosiloxanes containing hydroxyalkyl and in particular γ-hydroxypropyl functional groups, described in French Patent Application No. FR-8516334;

f) alkoxylated groups, as in Silicone copolymer F 755 from SWS Silicones and the products Abilwax® 2428, Abilwax® 2434 and Abilwaxe 2440 from the Company Goldschmidt;

g) acyloxyalkyl groups, such as, for example, the polyorganopolysiloxanes described in French Patent Application No. 88 17433, and in particular y-stearoyloxypropyl groups;

h) quaternaryammonium groups, as in the products X2 81 08 and X2 81 09 or the product Abil® K 3270 from the Company Goldschmidt;

i) amphoteric or betaine groups, such as in the product-sold by the Company Goldschmidt under the name Abil® B 9950;

The polyorganosiloxanes are present in composition, preferably personal care composition, in a proportion up to 50% by weight, based on the total weight of the composition. Preferably the polyorganosiloxanes are present from 0.2 to 50% by weight, more preferably between 1 and 30% by weight, based on the total weight of the composition.

Fluorinated or perfluorinated oils: perfluorhexane, dimethylcyclohexane, ethylcyclopentane (Flutec® grades). polyperfluoromethylisopropyl ether (Fomblin® grades) The oil components can be used in an amount of, for example, from 1 wt-% to 60 wt-%, especially from 5 wt-% to 50 wt-% and preferably from 10 wt-% to 35 wt-%, based on the total weight of the composition.

Emulsifiers. Any conventionally usable emulsifier can be used for the compositions. Emulsifier systems may comprise for example:

Carboxylic acids and their salts: alcalin soap of sodium, potassium and ammonium, metallic soap of calcium or magnesium, organic basis soap such as Lauric, palmitic, stearic and oleic acid etc . . .

Alkyl phosphates or phosphoric acid esters: acid phosphate, diethanolamine phosphate, potassium cetyl phosphate.

Ethoxylated Carboxylic Acids or Polyethyleneglycol esters (PEG-n Acylates). Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol Polyglycolether such as Laureth-n, Ceteareth-n, Steareth-n, Oleth-n. Fatty acid polyglycolether such as PEG-n Stearate, PEG-n Oleate, PEG-n Cocoate Monoglycerides and Polyol esters: $C_{12}-C_{22}$ fatty acid mono- and di-esters of addition products of from 1 to 30 mol of ethylene oxide with polyols Fatty acid and polyglycerol ester such as Monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as Monostearate diethylene glycol, Fatty acid and Polyethylene glycol esters, Fatty acid and saccharose esters such as Sucro esters, glycerol and saccharose esters such as Sucro glycerides Polyethoxylated fatty acid esters of sorbitan: Sorbitan mono- and di-esters of saturated and unsaturated fatty acids having from 6 to 22 carbon atoms and ethylene oxide addition products Polysorbate-n series, Sorbitan esters such as Sesquiisostearate, sorbitan, PEG-(6)-isostearate sorbitan, PEG-(10)-Sorbitan laurate, PEG-17-dioleate sorbitan.

Glucose derivatives: $C_8-C_{22}$ alkyl-mono and oligo-glycosides and ethoxylated analogues with glucose being preferred as the sugar component. O/W emulsifiers such as Methyl Gluceth-20 sesquistearate, Sorbitan Stearate/Sucrose Cocoate, Methyl Glucose Sesquistearate, Cetearyl alcohol/Cetearyl glucoside. W/O emulsifiers such as Methyl glucose Dioleate/Methyl glucose isostearate.

Sulfates and sulfonated derivatives: Dialkylsulfosuccinates (DOSS: Dioctyl succinate), alkyl lauryl sulfonate, linear sulfonated parafins, sulfonated tetrapropylene sulfonate, sodium lauryl sulfates, ammonium and ethanolamine lauryl sulfates, lauryl ether sulfates, sodium laureth sulfates, sulfosuccinates, acetyl isothionates, alkanolamide sulfates such as Taurines, Methyl taurines, Imidazole sulfates.

Amine derivatives: amine salts, ethoxylated amines such as Oxide amine, with chains containing an heterocycle such as alkylimidazolines, pyridine derivatives, isoquinoteines, cetyl pyridinium chlorure, cetyl pyridinium bromure, quaternary ammonium such as cetyltrimethylbromure ammonium bromure (CTBA), Stearylalkonium.

Amide derivatives.alkanolamides such as acylamide DEA, ethoxylated amides, such as PEG-n acylamide, oxydeamide.

Polysiloxane/Polyalkyl/Polyether Copolymers and derivatives: dimethicone, copolyols, silicone polyethylene Oxide copolymer, silicone glycol copolymer.

Propoxylated or POE-n Ethers (Meroxapols), Polaxamers or poly(oxyethylene)$_m$-block-poly(oxypropylene)$_n$-block(oxyethylene)

Zwitterionic surfactants that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having from 8 to 18 carbon atoms in the alkyl or acyl group and also cocoacylaminoethylhydroxyethyl-carboxy-methylglycinate, N-alkylbetaine, N-alkylaminobetaines. Alkylimidazolines, alkylopeptides, lipoaminoacides Self Emulsifying Bases (K. F. DePolo—A Short Textbook of Cosmetology, Chapter 8, Table 8-7, p250–251):

Non ionic bases such as PEG-6 Beeswax (and) PEG-6 Stearate (and) polyglyceryl-2 isostearate [Apifac], Glyceryl stearate (and) PEG-100 stearate. [Arlacel 165], PEG-5 Glyceryl stearate [Arlatone 983 S], Sorbitan oleate (and) Polyglyceryl-3 Ricinoleate.[Arlacel 1689], Sorbitan Stearate and sucrose cocoate [arlatone 2121], Glyceryl stearate and laureth-23 [Cerasynth 945], Cetearyl alcohol and ceteth-20 [Cetomacrogol Wax], Cetearyl alcohol and Polysorbate 60 and PEG-150 and stearate-20[Polawax GP 200, Polawax NF], Cetearyl alcohol and cetearyl polyglucoside [Emulgade PL 1618], Cetearyl alcohol and ceteareth-20 [Emulgade 1000NI, Cosmowax], Cetearyl alcohol and PEG-40 castor oil [Emulgade F Special], Cetearyl Alcohol and PEG-40 Castor Oil and Sodium Cetearyl Sulfate [Emulgade F], Stearyl Alcohol and Steareth-7 and Steareth-10 [Emulgator E 2155], Cetearyl Alcohol and Szeareth-7 and steareth-10 [Emulsifying wax U.S.N.F], Glyceryl stearate and PEG-75 stearate [Gelot 64], Propylene Glycol ceteth-3 Acetate [Hetester PCS], Propylene Glycol isoceth-3 Acetate [Hetester PHA], Cetearyl alcohol and Ceteth-12 and oleth-12 [Lanbritol Wax N 21], PEG-6 Stearate and PEG-32 Stearate [Tefose 1500], PEG-6 Stearate and ceteth-20 and steareth-20 [Tefose 2000], PEG-6 Stearate and ceteth-20 and Glyceryl Stearate and steareth-20 [Tefose 2561], Glyceryl Stearate and ceteareth-20 [Teginacid H, C, X].

Anionic alkaline bases such as PEG-2 Stearate SE, Glyceryl stearate SE [Monelgine, Cutina KD], Propylene glycol stearate [Tegin P].

Anionic acid bases such as Cetearyl Alcohol and Sodium cetearyl sulfate [Lanette N, Cutina LE, Crodacol GP], Cetearyl Alcohol and sodium Lauryl Sulfate [Lanette W], Trilaneth-4 Phosphate and glycol stearate and PEG-2 Stearate [Sedefos 75], Glyceryl stearate and sodium lauryl Sulfate [Teginacid Special].

Cationic acid bases such as cetearyl Alcohol and cetrimonium bromide.

The emulsifiers may be used in an amount of, for example, from 1 wt-% to 30 wt-%, especially from 4 wt-% to 20 wt-% and preferably from 5 wt-% to 10 wt-%, based on the total weight of the composition.

When formulated in O/W emulsions, the preferably amount of such emulsifier system could represent 5% to 20% of the oil phase.

Adjuvants and additives. The UV-protection formulation, for example creams, gels, lotions, alcoholic and aqueous/alcoholic solutions, emulsions, wax/fat compositions, stick preparations, powders or ointments, may in addition contain, as further adjuvants and additives, mild surfactants, superfatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Super-fatting agents. Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants. Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isothionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency regulators/Thickeners and Rheology modifiers. As thickeners and rheology modifiers, there come into consideration the groups of silicium dioxide, magnesium silicates, aluminium silicates, polysaccharides or derivatives thereof for example hyaluronic acid, xanthan gum, guar-guar, agar-agar, alginates, Carraghenan, gellan, pectines, or modified cellulose such as hydroxycellulose, hydroxypropylmethylcellulose. In addition polyacrylates or homopolymer of reticulated acrylic acids and polyacrylamides, e.g. the Carbopol range (e.g. Carbopol types 980, 981, 1382, ETD 2001, ETD2020, Ultrez 10; INCI: Carbomer) or Salcare range such as Salcare SC80(Steareth-10 Allyl Ether/Acrylates Copolymer), Salcare SC81 (Acrylates copolymer), Salcare SC91 and Salcare AST(Sodium Acrylates Copolymer/PPG-1 trideceth-6), Sepigel 305(Polyacrylamide/laureth-7), Simulgel NS and Simulgel EG (Hydroxyethyl Acrylate/Sodium Acryloyldimethyl Taurate Copolymer), Stabilen 30 (Acrylates/Vinyl Isodecanoate Crosspolymer), Pemulen TR-1 (Acrylates/$C_{10}$–$C_{30}$ Alkyl Acrylate Crosspolymer), Luvigel EM (Sodium Acrylates Copolymer), Aculyn 28(Acrylates/Beheneth-25 Methacrylate Copolymer), etc.

Polymers. Suitable cationic polymers are, for example, cationic cellulose derivatives, for example a quaternised hydroxymethyl cellulose obtainable under the name Polymer JR 400® from Amerchol, cationic starches, copolymers of diallylammonium salts and acrylamides, quaternised vinylpyrrolidone/vinyl imidazole polymers, for example Luviquat® (BASF), condensation products of polyglycols and amines, quaternised collagen polypeptides, for example lauryidimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyldiethylene-triamine (Cartaretin®/Sandoz), copolymers of acrylic acid with dimethyldiallylammonium chloride (Merquat® 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethyl-aminoethyl methacrylate/vinyl caprolactam terpolymers and also optionally derivatised cellulose ethers and silicones. Furthermore the polymers as described in EP 1093796 (pages 3–8, paragraphs 17–68) may be used.

Biogenic active ingredients. Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising active ingredients. As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® Henkel KGaA, Düsseldorf/FRG), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5–Chloro-2-(2,4-dichlorophenoxy)-phenol (Irgasan®, Ciba Specialty Chemicals Inc.) has also proved especially effective.

Anti-dandruff agents. As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants. In addition to the primary light-protective substances it is also possible to use secondary light-protective substances of the antioxidant kind that interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. β-carotene, β-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. α-hydroxy fatty acids, palmitic acid phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, butyl hydroxyanisole, nordihydroguaiaretic acid, trihydroxy-butyrophenone, uric acid and derivatives thereof, mannose and derivatives thereof, superoxide dismutase, N-[3-(3,5-di-tert-butyl-4-hydroxyphenyl) propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 wt-% to 30 wt-%, preferably from 0.01 wt-% to 3 wt-%, based on the weight of the UV absorber(s).

Hydrotropic agents. To improve the flow behaviour it is also possible to employ hydrotropic agents, for example ethoxylated or non ethoxylated mono-alcohols, diols or polyols with a low number of C-atoms or their ethers (e.g. ethanol, isopropanol, 1,2-dipropanediol, propyleneglycol, glycerine, ethylene glycol, ethylene glycol, monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 wt-% to 50 wt-%; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-inhibiting agents. Suitable preservatives include, for example, methyl-, ethyl-, propyl-, butyl- parabens, Benzalkonium chloride, 2-Bromo-2-nitropropane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea and Triclosan . . . and further substance classes listed in the following reference: K.:F.DePolo—A short textbook of cosmetology, Chapter 7, Table 7-2,7-3, 7-4 and 7-5, p210–219.

Bacteria-inhibiting agents. Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2, 6,10-dodecatrien-1-ol), which is present in lime blossom oil. Glycerol monolaurate has also proved to be a bacteriostatic agent. The amount of the additional bacteria-inhibiting agents present is usually from 0.1 wt-% to 2 wt-%, based on the solids content of the preparations.

Perfume oils. There may be mentioned as perfume oils mixtures of natural and/or synthetic aromatic substances. Natural aromatic substances are, for example, extracts from blossom (lilies, lavender, roses, jasmine, neroli, ylangylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α,α-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, α-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colourants. There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 wt-% to 0.1 wt-%, based on the total mixture.

Other adjuvants. It is furthermore possible for the UV-protection formulation to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

There come into consideration as insect repellents, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Polymeric beads or hollow spheres as SPF enhancers. The combination of the UV-absorbers described above, with SPF enhancers, such as non-active ingredients like Styrene/acrylates copolymer, silica beads, spheroidal magnesium silicate, spherical polyamide powder such as n-lactam polymer (Orgasol® range, Elf Atochem) crosslinked Polymethylmethacrylates (PMMA; Micopearl M305 Seppic), can maximize better the UV protection of the sun products. Holosphere additives (Sunspheres® ISP, Silica Shells Kobo.) deflect radiation and the effective path length of the photon is therefore increased. (EP0893119). Some beads, as mentioned previously, provide a soft feel during spreading. Moreover, the optical activity of such beads, e.g. Micropearl M305, cans modulate skin shine by eliminating reflection phenomena and indirectly,may scatter the UV light. When formulated in O/W emulsions, the preferably amount of such SPF enhancers should represent 1% to 10% of the total amount of the emulsion.

Cosmetic or pharmaceutical preparations. UV-protection formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation forms. The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or
in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Other typical ingredients in such UV-protection formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulgators or emulsifying surfactants, surfactants, dispersing agents, antioxidants, anti-irritants and anti-inflammatory agents etc.

An especially preferred embodiment of the present invention is a UV-protection formulation comprising from 0.1 wt-% up to 10 wt-%, more preferably 0.5 wt-% up to 5 wt-%, of a compound of the following formula or a mixture thereof

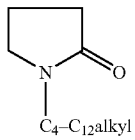

and from 0.05 wt-% to 40 wt-%, preferably from 0.1 wt-% to 20 wt-% and especially from 0.5 wt-% to 10 wt-%, of a compound of formula (1) to (16) or a mixture thereof and of further adjuvants to a total of 100 wt-%.

An further especially preferred embodiment of the present invention is a UV-protection formulation comprising from 0.05 wt-% up to 10 wt-%, more preferably 0.5 wt-% up to 5 wt-%, of a compound of the following formula or a mixture thereof

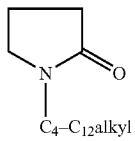

and from 0.1 wt-% to 40 wt-%, preferably from 0.1 wt-% to 20 wt-% and especially from 0.5 wt-% to 10 wt-%, of a compound of formula (1) to (16) or a mixture thereof and up to 20 wt-% (preferably about 2.5—about 10 wt-%) of an ether compound or a mixture there of as defined above and of further adjuvants to a total of 100 wt-%.

Example of a Water/Oil Emulsifier System
(a) 3.5 wt-% of a $C_{12}$–$C_{15}$alkylbenzoate (for example Tegosoft® TN)
(b) 1,50 wt-% of a microcrystalline wax (for example Permulgin® 4200)
(c) 3.5 wt-% of a mineral oil (for example Paraffin)
(d) 3.5 wt-% of isohexadecane
(e) 2.5 wt-% of a UV absorber of formula (8)
(f) 5.0 wt-% of capric triglyceride
(g) 1.5 wt-% of Finsolv® TPP
(h) 1.0 wt-% of caprylyl pyrrolidone (compound of formula (I) or (Ia))
(i) 0.8 wt-% of a hydrogenated castor oil (for example Tegosoft® CH)
(j) 3.5 wt-% of a PEG-30 dipolyhydroxystearate (for example Arlacel® P135)
(k) 1.5 wt-% of a PEG-22/dodecyl glycol copolymer (for example Elfacos® ST37)
(l) 4.0 wt-% of propylene glycol
(m) 0.7 wt-% of $MgSO_4$ $7H_2O$
(n) 2.0 wt-% of glycerin
(o) water
(p) 0.5 wt-% of mixture of diazolidinyl urea and methyl paraben and propyl paraben and propylene (for Germaben® II)

To receive a smooth and yellowish cream parts (a)-(k) are mixed and heated up to 80° C. The mixture is added to a mixture containing parts (l)-(o), which was heated up to 80° C. as well. This mixture is homogenised for about 10s at 10'000 rpm. Finely part (p) is added to the formulation. The obtained UV-protection formulation has a viscosity of 25000-30000 mPas (measured by Brookfield DVIII+LV4/RT/5 rpm)

Example of Oil/Water Emulsifier System
(a) 6.0 wt-% of a $C_{12}$–$C_{15}$alkylbenzoate (for example Tegosoft® TN)
(b) 2.0 wt-% of capric triglyceride
(c) 1.5 wt-% caprylyl pyrrolidone (compound of formula (I) or (Ia))
(d) 3.5 wt-% of cetearyl alcohol/dicetyl phosphate/ceteth-10 phosphate (for example Crodafos® CES)
(e) 7.0 wt-% of a UV absorber of formula (8)
(f) 2.0 wt-% of cetearyl octanoate/isopropyl myristate (for example Crodamol® CAP)
(g) 1.5 wt-% of stearic acid
(h) 2.5 wt-% of glyceryl stearate
(i) water
(j) 0.2 wt-% of sodium acrylates copolymer and glycine soja and PPG-1 trideceth-6 (for example Salcare® AST)
(k) 0.15 wt-% of a mixture of diazolidinyl urea and iodopropynyl butylcarbamate (for example Germall® Plus)
(l) 3.5 wt-% of propylene glycol
(m) 0.15 wt-% of sodium hydroxide To receive a smooth and yellow cream parts (a)-(h) are mixed and heated up to 75° C. Water having a temperature of 75° C. is added under stirring. Part 0) is added and this mixture is homogenised for about 10s at 10'000 rpm. Finally, parts (k) and (l) are added to the formulation. The formulation is cooled down to room temperature under stirring. The ph value is adjusted to 6.0 to 6.5 by adding part (m). The final mixture is homogenised for about 10s at 16'000 rpm.

The obtained UV-protection formulation has a viscosity of 30000–40000 mPas (measured by Brookfield DVIII+LV4/RT/5 rpm)

Example of Oil/Water Emulsifier System
(a) 6.0 wt-% of a $C_{12}$–$C_{15}$alkylbenzoate (for example Tegosoft® TN)
(b) 2.0 wt-% of capric triglyceride
(c) 1.5 wt-% caprylyl pyrrolidone (compound of formula (I) or (Ia))
(d) 3.5 wt-% of cetearyl alcohol/dicetyl phosphate/ceteth-10 phosphate (for example Crodafos® CES)
(e) 5.0 wt-% of a UV absorber of formula (8)

(f) 2.0 wt-% of cetearyl octanoate/isopropyl myristate (for example Crodamol® CAP)
(g) 1.5 wt-% of stearic acid
(h) 2.5 wt-% of glyceryl stearate
(i) water
(j) 0.2 wt-% of sodium acrylates copolymer and glycine soja and PPG-1 trideceth-6 (for example Salcare® AST)
(k) 0.15 wt-% of a mixture of diazolidinyl urea and iodopropynyl butylcarbamate (for example Germall® Plus)
(l) 3.5 wt-% of propylene glycol
(m) 0.15 wt-% of sodium hydroxide To receive a smooth and yellow cream parts (a)-(h) are mixed and heated up to 75° C. Water having a temperature of 75° C. is added under stirring. Part (j) is added and this mixture is homogenised for about 10s at 10'000 rpm. Finally, parts (k) and (l) are added to the formulation. The formulation is cooled down to room temperature under stirring. The ph value is adjusted to 6.0 to 6.5 by adding part (m). The final mixture is homogenised for about 10s at 16'000 rpm.

The obtained UV-protection formulation has a viscosity of 30000–40000 mPas (measured by Brookfield DVIII+ LV4/RT/5 rpm)

Example of a Water/Oil Emulsifier System
(a) 6.0 wt-% of a $C_{12}$–$C_{15}$alkylbenzoate (for example Tegosoft® TN)
(b) 1,50 wt-% of a microcrystalline wax (for example Permulgin® 4200)
(c) 4.0 wt-% of a mineral oil (for example Paraffin)
(d) 4.0 wt-% of isohexadecane
(e) 4.0 wt-% of a UV absorber of formula (8)
(f) 6.0 wt-% of capric triglyceride
(g) 3.5 wt-% of diisostearoyl polyglyceryl-3 diisostearate (for example Isolan® PDI)
(h) 1.5 wt-% of caprylyl pyrrolidone (compound of formula (I) or (Ia))
(i) 0.8 wt-% of a hydrogenated castor oil (for example Tegosoft® CH)
(j) 4.0 wt-% of propylene glycol
(k) 0.7 wt-% of $MgSO_4$ $7H_2O$
(l) 2.0 wt-% of glycerin
(m) water
(n) 0.5 wt-% of mixture of diazolidinyl urea and methyl paraben and propyl paraben and propylene (for Germaben® II)

To receive a smooth and yellowish cream parts (a)-(i) are mixed and heated up to 80° C. The mixture is added to a mixture containing parts (j)-(m), which was heated up to 80° C. as well. This mixture is homogenised for about 10s at 10'000 rpm. Finely part (l) is added to the formulation.

The obtained UV-protection formulation has a viscosity of 25000–30000 mPas (measured by Brookfield DVIII+ LV4/RT/5 rpm)

Example of a Water/Oil Emulsifier System
(a) 1.5 wt-% of a microcrystalline wax (for example Permulgin® 4200)
(b) 6.0 wt-% of a mineral oil (for example Paraffin)
(c) 3.0 wt-% of isohexadecane
(d) 2.5 wt-% of a UV absorber of formula (8)
(e) 3.75 wt-% of diisostearoyl polyglyceryl-3 diisostearate (for example Isolan® PDI)
(f) 1.5 wt-% of caprylyl pyrrolidone (compound of formula (I) or (Ia))
(g) 0.8 wt-% of a hydrogenated castor oil (for example Tegosoft® CH)
(h) 8.0 wt-% of dipropylene glycol dibenzoate
(i) 4.0 wt-% of propylene glycol
(j) 0.7 wt-% of $MgSO_4$ $7H_2O$
(k) 2.0 wt-% of glycerin
(l) water
(m) 0.5 wt-% of mixture of diazolidinyl urea and methyl paraben and propyl paraben and propylene (for Germaben® II)

To receive a smooth and yellowish cream parts (a)-(h) are mixed and heated up to 80° C. The mixture is added to a mixture containing parts (i)-(l), which was heated up to 80° C. as well. This mixture is homogenised for about 10s at 10'000 rpm. Finely part (m) is added to the formulation.

The obtained UV-protection formulation has a viscosity of 90'000–100'000 mPas (measured by Brookfield DVIII+ LV4/RT/5 rpm)

The following Examples further illustrate the present invention. Parts and percentages shown therein are by weight unless otherwise stated.

EXAMPLE 1–5

In the following Examples 1–5, always two UV-protection formulations have been prepared. In each formulation a compound of the following formula

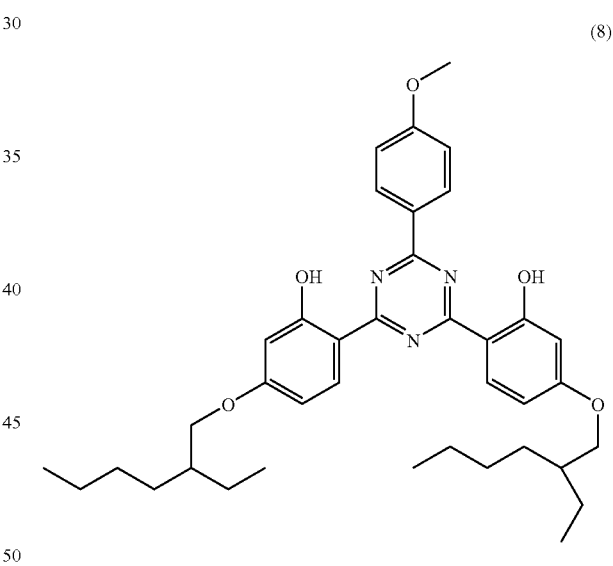

(8)

has been used as UV absorber.

The first of each Example (a) contains a compound of formula (I) whereas the (b)-Example does not contain such a compound. Both formulations have been stored for 2 weeks, respectively for 1 month at room temperature. After these periods, the formulations have been examined under the microscope (125×-magnification).

EXAMPLE 1a

A formulation containing 4 wt-% of a compound according to formula (8) and 1.5 wt-% of a compound of formula (Ib)

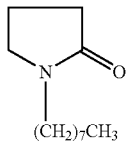

is prepared.

EXAMPLE 1b

A formulation containing 4 wt-% of a compound according to formula (8) is prepared.

EXAMPLE 2a

A formulation containing 2.5 wt-% of a compound according to formula (8) and 1.5 wt-% of a compound of formula (Ib) is prepared.

EXAMPLE 2b

A formulation containing 2.5 wt-% of a compound according to formula (8) is prepared.

EXAMPLE 3a

A formulation containing 2.5 wt-% of a compound according to formula (8) and 1.0 wt-% of a compound of formula (Ib) is prepared.

EXAMPLE 3b

A formulation containing 2.5 wt-% of a compound according to formula (8) is prepared.

EXAMPLE 4a

A formulation containing 4 wt-% of a compound according to formula (8) and 1.5 wt-% of a compound of formula (Ib) is prepared.

EXAMPLE 4b

A formulation containing 4 wt-% of a compound according to formula (8) is prepared.

EXAMPLE 5a

A formulation containing 7 wt-% of a compound according to formula (8) and 1.5 wt-% of a compound of formula (Ib) is prepared.

EXAMPLE 5b

A formulation containing 7 wt-% of a compound according to formula (8) is prepared.

TABLE 1

| Example | 2 weeks | 1 month |
| --- | --- | --- |
| 1a | no crystallization | start of sparingly crystallization |
| 1b | crystallization | strong crystallization |
| 2a | no crystallization | no crystallization |

TABLE 1-continued

| Example | 2 weeks | 1 month |
| --- | --- | --- |
| 2b | start of crystallization | strong crystallization |
| 3a | no crystallization | no crystallization |
| 3b | crystallization | strong crystallization |
| 4a | no crystallization | no crystallization |
| 4b | crystallization | strong crystallization |
| 5a | no crystallization | no crystallization |
| 5b | crystallization | strong crystallization |

The results of these comparison tests show clearly, that without the addition of a compound of formula (I) the UV-protection formulation is significantly less stable against crystallization.

What is claimed is:

1. A UV-protection formulation composition comprising a compound of formula (I) or a mixture thereof

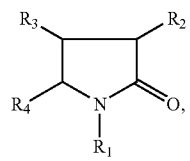

wherein
 $R_1$ is substituted or unsubstituted $C_6$–$C_{12}$alkyl, and
 $R_2$, $R_3$ and $R_4$ are independently from each other hydrogen; substituted or unsubstituted $C_1$–$C_4$alkyl.

2. A UV-protection formulation composition according to claim 1 wherein $R_2$, $R_3$ and $R_4$ are independently from each other hydrogen; unsubstituted $C_1$–$C_2$alkyl or substituted $C_1$–$C_2$alkyl.

3. A UV-protection formulation composition according to claim 1 wherein $R_2$, $R_3$ and $R_4$ are hydrogen.

4. A UV-protection formulation according to claim 1, comprising from 0.1 wt-% up to 10 wt-% of a compound of formula (I) or a mixture thereof.

5. A UV-protection formulation according to claim 4, comprising from 0.5 wt-% up to 5 wt-% of a compound of formula (I) or a mixture thereof.

6. A UV-protection formulation according to claim 1, comprising in addition an ether or polyether compound or a mixture thereof.

7. A UV-protection formulation according to claim 6 wherein the ether or polyether is
 (i) A-O-B,
  wherein A and B are independently from each other $C_1$–$C_{10}$alkyl; $C_1$–$C_4$alkylene-O—$C_1$–$C_8$alkyl or $C_1$–$C_4$alkylene-O—($C_1$–$C_4$alkylene-O-)$_{1-4}$$C_1$–$C_8$alkyl, wherein the alkyl and alkylene groups may be linear or branched and optionally substituted by at least one substituent of the group consisting of CN, OH, halogen or $NH_2$;
 (ii) a methoxycinnamate derivate; or
 (iii) cyclic; or
 (iv) a silicone-containing derivative,
as well as mixtures thereof.

8. A UV-protection formulation according to claim 1, comprising at least one compound according to formulae (II) to (XI)

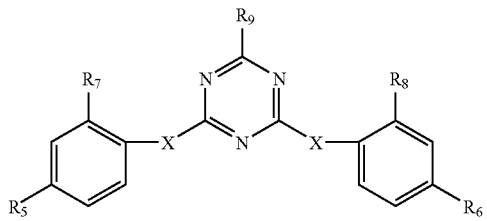
(II)

in which

X is —NR$_{10}$— or a direct bond, in which
R$_{10}$ is hydrogen; C$_1$–C$_4$alkyl or substituted C$_1$–C$_4$alkyl, R$_5$ and R$_6$, independently of one another, are OC$_3$–C$_{18}$alkyl; OC$_2$–C$_{18}$alkenyl; a radical of the formula O—CH$_2$—CH(—OH)—CH$_2$—$_{O-T1}$; COOC$_3$–C$_{18}$alkyl; NR$_{10}$OC$_3$–C$_{18}$alkyl, wherein T$_1$ is hydrogen or C$_1$–C$_8$alkyl and R$_{10}$ is as defined above, or R$_5$ and R$_6$ are a radical of the formula (1a)

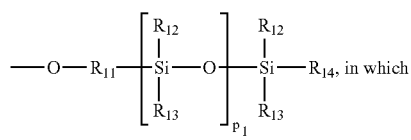

R$_{11}$ is a direct bond; a straight-chain or branched C$_1$–C$_4$alkylene radical or a radical of the formula

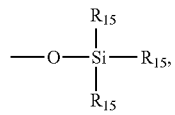

R$_{15}$ is C$_1$–C$_5$alkyl, each m$_1$ is independently of one another 1 to 4, p$_1$ is 0 or a number from 1 to 5, R$_7$ and R$_8$ are independently from each other H; OH or OC$_1$–C$_5$alkyl, R$_9$ is COOC$_3$–C$_{18}$alkyl; NR$_{10}$OC$_3$–C$_{18}$alkyl, wherein R$_{10}$ is as defined above, or R$_9$ is a radical of the formula

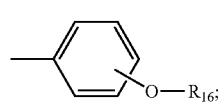
(1b)

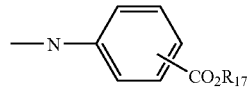
(1c)

or of the formula

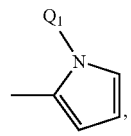
(1d)

wherein

R$_{16}$ is hydrogen; C$_1$–C$_{10}$alkyl; —(CH$_2$CHR$_{18}$—O)$_{n1}$—R$_{17}$ or a radical of the formula

—CH$_2$—CH(—OH)—CH$_2$—O-T$_1$

R$_{17}$ is hydrogen; M; C$_1$–C$_5$alkyl or a radical of the formula —(CH$_2$)$_{m2}$—O-T$_1$, R$_{18}$ is hydrogen or methyl, is hydrogen or C$_1$–C$_8$alkyl, Q$_1$ C$_1$–C$_{18}$alkyl, M is a metal cation, m$_2$ is 1 to 4, and n$_1$ is 16;

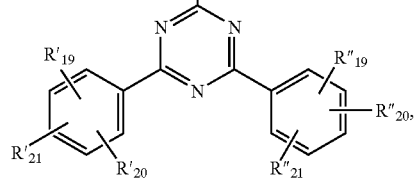
(III)

wherein

R$_{19}$, R'$_{19}$, R"$_{19}$, R$_{20}$, R'$_{20}$ and R"$_{20}$ are each independently of the other hydrogen; hydroxy; C$_1$–C$_{12}$alkyl; OC$_1$–C$_{12}$alkyl; OC$_2$–C$_{18}$alkenyl or OC$_1$–C$_4$alkylenephenyl, and R$_{21}$, R'$_{21}$ and R"$_{21}$ are each independently of the other C$_1$–C$_{12}$alkyl or C$_1$–C$_{12}$alkoxy;

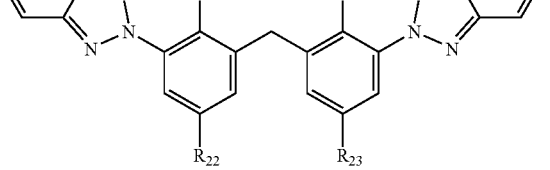
(IV)

wherein

R$_{22}$ and R$_{23}$ independently from each other signify C$_1$–C$_{12}$alkyl;

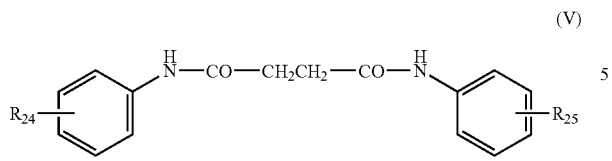
(V)

in which
R$_{24}$ and R$_{25}$, independently from each other, are C$_1$–C$_{18}$alkyl or C$_1$–C$_{18}$alkoxy;

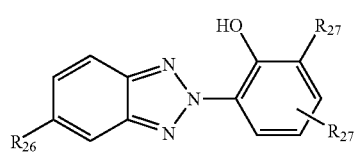
(VI)

in which
R$_{26}$ is C$_1$–C$_{16}$alkyl or hydrogen, and
R$_{27}$ is C$_1$–C$_{18}$alkyl, optionally substituted by phenyl;

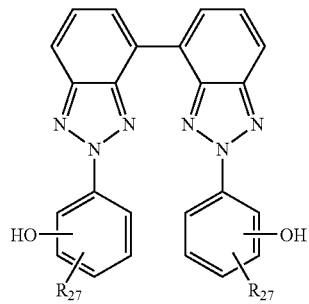
(VII)

in which R$_{27}$ has its previous significance;

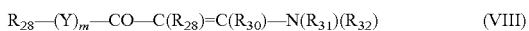
(VIII)

in which R$_{28}$ is C$_1$–C$_{18}$alkyl or phenyl optionally substituted by one, two or three substituents selected from OH, C$_1$–C$_{18}$alkyl, C$_1$–C$_{18}$alkoxy or CO—OR$_{33}$, in which
R$_{33}$ is C$_1$–C$_{18}$alkyl,
R$_{29}$, R$_{30}$, R$_{31}$ and R$_{32}$ are the same or different and each is C$_1$–C$_{18}$alkyl or hydrogen,
Y is N or O, and
m is 0 or 1;

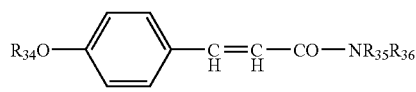
(IX)

in which R$_{34}$ is hydroxy or C$_1$–C$_4$alkoxy,
R$_{35}$ is hydrogen or C$_1$–C$_4$alkyl, and
R$_{36}$ is —(CONH)$_m$-phenyl in which m has its previous significance and the phenyl group is optionally substituted by one, two or three substituents selected from OH, C$_1$–C$_{18}$alkyl, C$_1$–C$_{18}$alkoxy or COOR$_{33}$ in which R$_{33}$ has its previous significance;

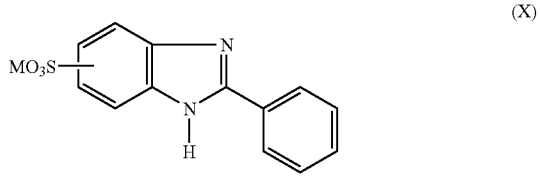
(X)

in which
M is hydrogen, an alkali metal, an alkaline earth metal or zinc;

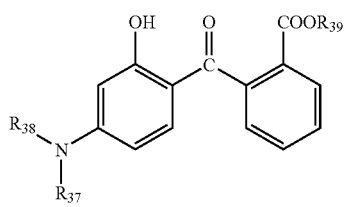
(XI)

wherein
R$_{37}$ and R$_{38}$ signify independently from each other H; unsubstituted C$_1$–C$_{20}$alkyl; substituted C$_1$–C$_{20}$alkyl; unsubstituted C$_3$–C$_{10}$-cycloalkyl; substituted C$_3$–C$_{10}$-cycloalkyl; unsubstituted C$_3$–C$_{10}$-cycloalkenyl or substituted C$_3$–C$_{10}$-cycloalkenyl,
or R$_{37}$ and R$_{38}$ form together with the nitrogen atom to which they are bound a 5 or 6 membered ring, and
R$_{39}$ signifies unsubstituted C$_1$–C$_{20}$alkyl or substituted C$_1$–C$_{20}$alkyl.

9. A UV-protection formulation according to claim 8, comprising at least one compound according to formula (II), (III) and/or formula (XI).

10. A UV-protection formulation according to claim 8, comprising at least one compound according to formula (IIa)

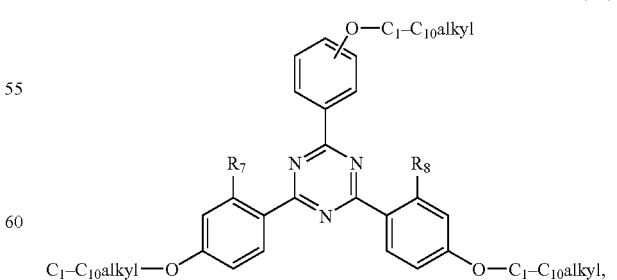
(IIa)

wherein,
R$_7$ and R$_8$ are independently from each other H; OH or OC$_1$–C$_5$alkyl, and/or at least one compound according to formula (IIb)

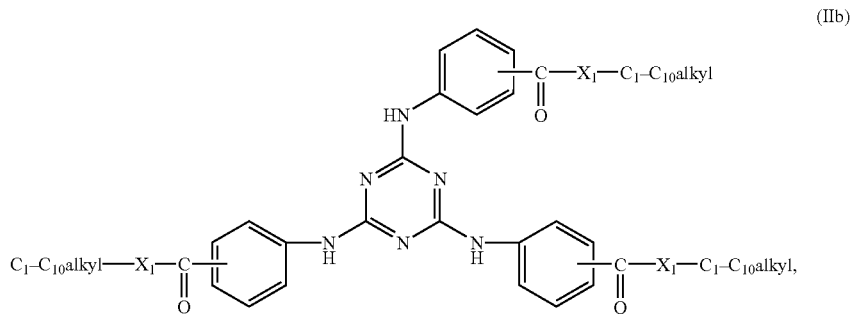

wherein $X_1$ signifies —O— or —NH—, and/or
at least one compound according to formula (IIIa)

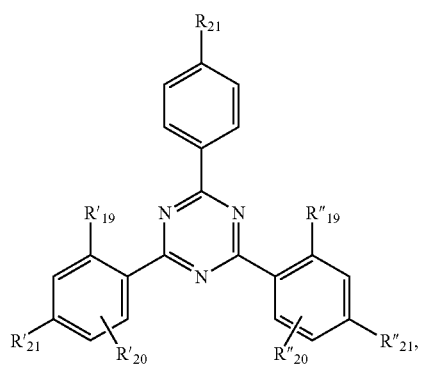

wherein
$R'_{19}$, $R''_{19}$, $R'_{20}$ and $R''_{20}$ are independently from each other hydrogen; hydroxy; $C_1$–$C_{12}$alkyl or $C_1$–$C_{12}$alkyoxy, and
$R_{21}$, $R'_{21}$ and $R''_{21}$ are independently from each other hydroxy; $C_1$–$C_{12}$alkyl or $C_1$–$C_{12}$alkoxy, and/or
at least one compound according to formula (IIIb)

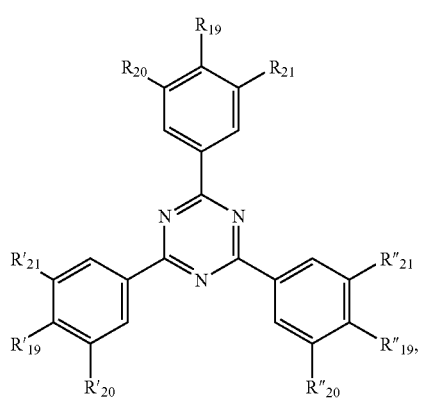

wherein
$R_{19}$, $R'_{19}$ and $R''_{19}$ are independently from each other hydroxy or $C_1$–$C_{12}$alkyoxy, and $R_{20}$, $R'_{20}$ and $R''_{20}$ are independently from each other hydroxy or $C_1$–$C_{12}$alkyl, and
$R_{21}$, $R'_{21}$ and $R''_{21}$ are independently from each other hydrogen or $C_1$–$C_{12}$alkyl, and/or
at least one compound according to formula (XIa)

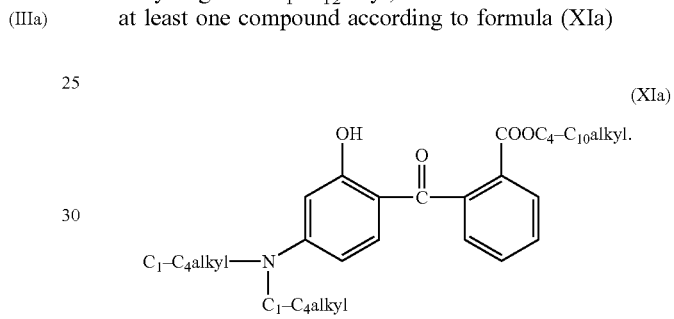

11. A UV-protection formulation according to claim 8, comprising from about 0.05 wt-% to about 40 wt-% based on the total weight of the composition, of one or more compounds according to formula (II)–(XI).

12. A UV-protection formulation according to claim 1, additionally comprising fatty alcohols, esters of fatty acids, hydrocarbon oils, silicones, siloxanes, fluorinated oils, perfluorinated oils and/or emulsifiers.

13. A UV-protection formulation according to claim 12, comprising further adjuvants.

14. A UV-protection formulation according to claim 13, wherein the adjuvants are mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants and/or bacteria-inhibiting agents.

15. A UV-protection formulation comprising from 0.1 wt-% up to 10 wt-% compound of the following formula or a mixture thereof

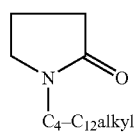

and from 0.05 wt-% to 40 wt-% of a compound of formula (1) to (16) or a mixture thereof

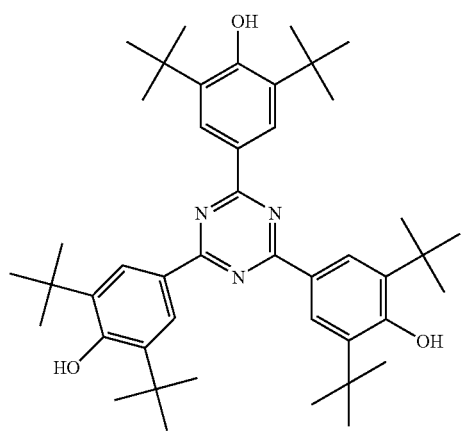
(1)
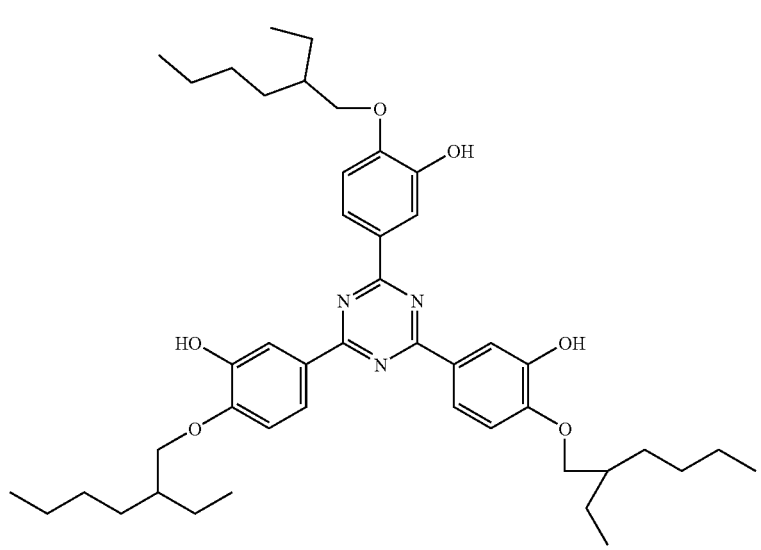
(2)
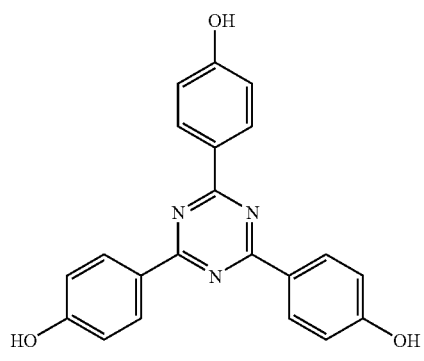
(3)
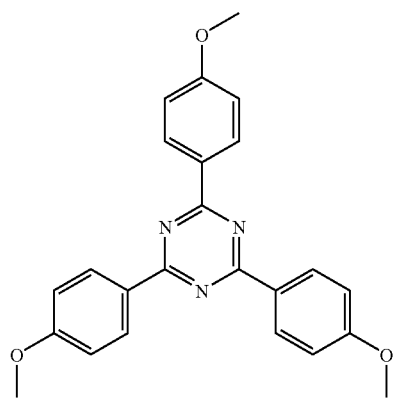
(4)

-continued
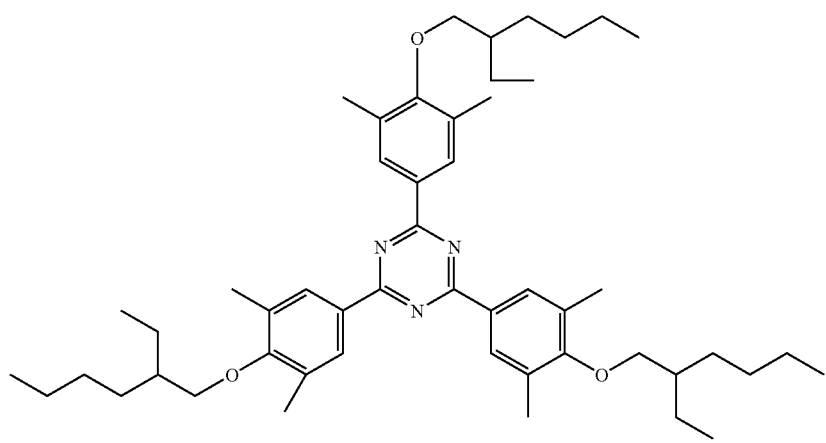
(5)
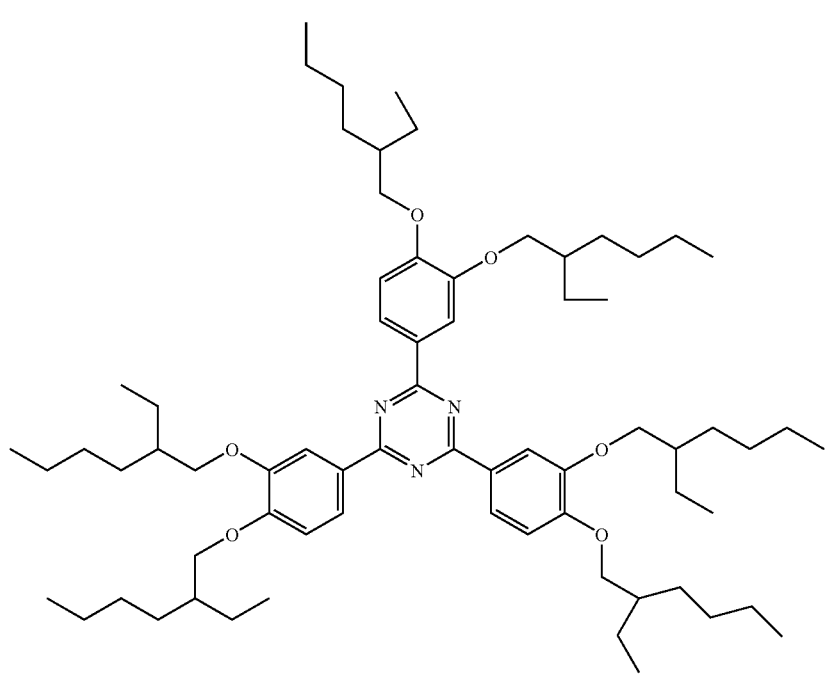
(6)
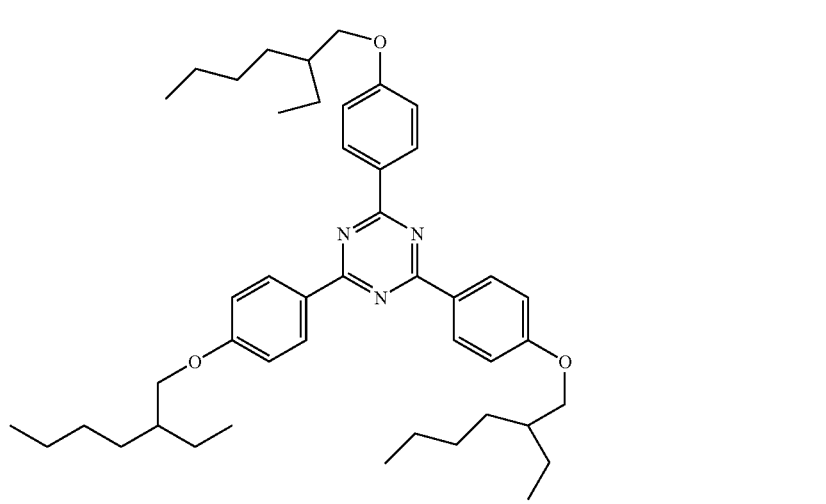
(7)

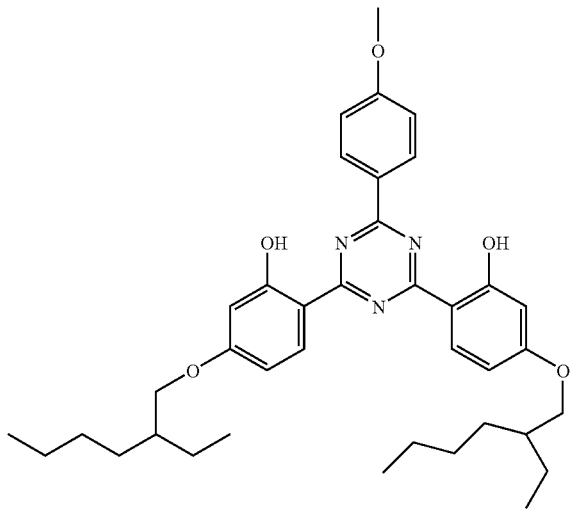
(8)
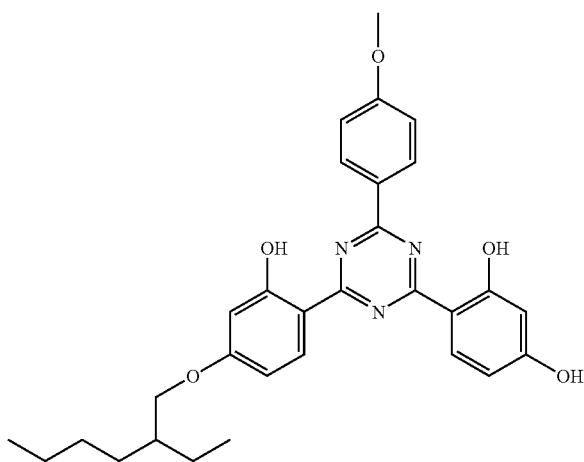
(9)
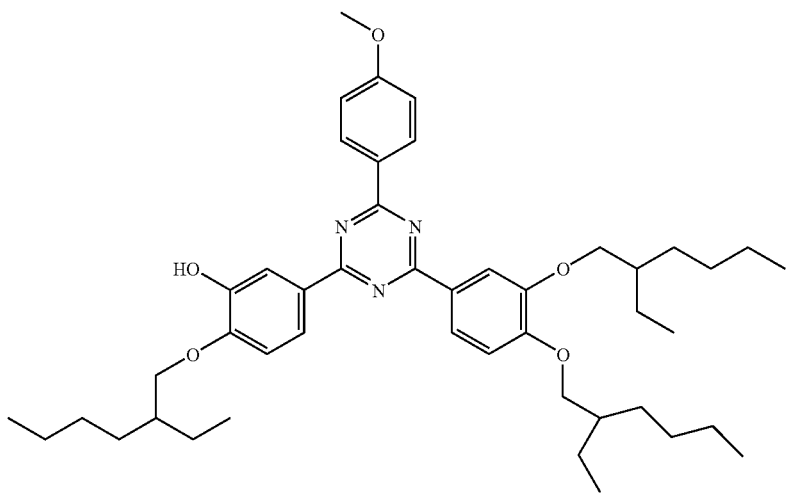
(10)

-continued
(11)
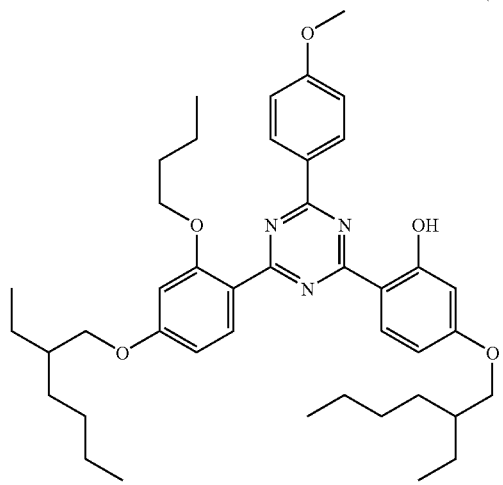
(12)
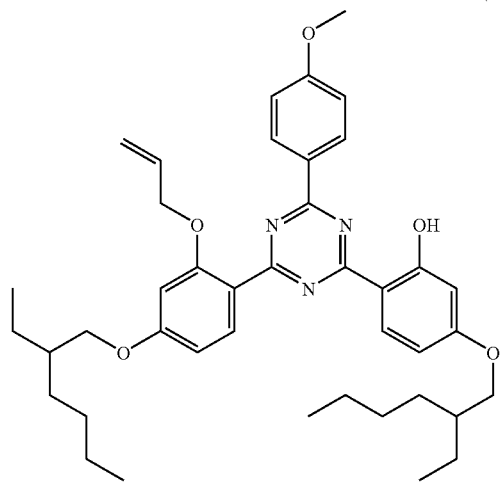
(13)
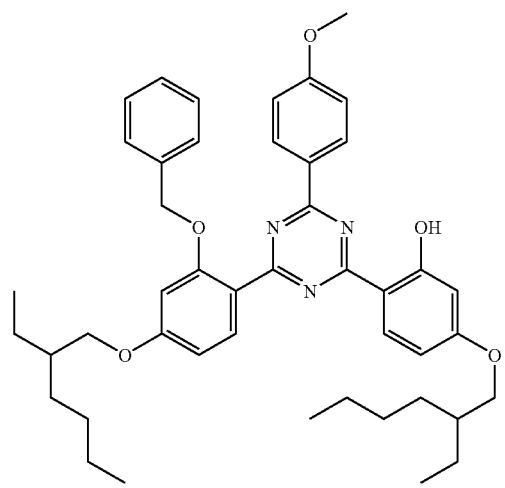
(14)
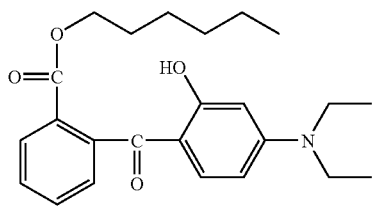
(15)
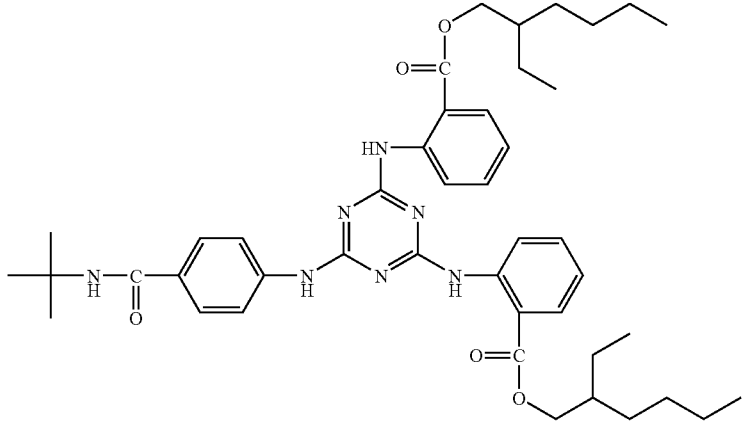

-continued
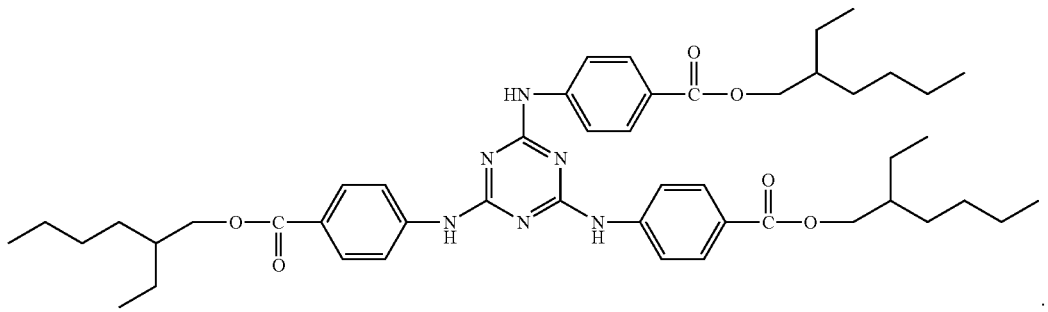
(16)
* * * * *